(12) United States Patent
Richter

(10) Patent No.: US 9,039,755 B2
(45) Date of Patent: May 26, 2015

(54) HELICAL HYBRID STENT

(71) Applicant: Medinol Ltd., Tel Aviv (IL)

(72) Inventor: Jacob Richter, Arsuf (IL)

(73) Assignee: Medinol Ltd., Tel Aviv (IL)

( * ) Notice: Subject to any disclaimer, the term of this patent is extended or adjusted under 35 U.S.C. 154(b) by 87 days.

(21) Appl. No.: 13/829,153

(22) Filed: Mar. 14, 2013

(65) Prior Publication Data

US 2013/0204350 A1 Aug. 8, 2013

Related U.S. Application Data

(63) Continuation-in-part of application No. 13/467,800, filed on May 9, 2012, which is a continuation of application No. 12/428,347, filed on Apr. 22, 2009, now Pat. No. 8,382,821, which is a (Continued)

(51) Int. Cl.
*A61F 2/88* (2006.01)
*A61F 2/89* (2013.01)
(Continued)

(52) U.S. Cl.
CPC ............... *A61F 2/89* (2013.01); *A61L 31/022* (2013.01); *A61L 31/10* (2013.01); *A61F 2/88* (2013.01); *A61F 2/91* (2013.01); *A61F 2250/0068* (2013.01); *A61F 2/90* (2013.01);
(Continued)

(58) Field of Classification Search
CPC .................................... A61F 2/88; A61F 2/89
USPC ....................................................... 623/1.22
See application file for complete search history.

(56) References Cited

U.S. PATENT DOCUMENTS

| 3,986,867 A | 10/1976 | Masumoto et al. |
| 4,017,911 A | 4/1977 | Kafesjian et al. |

(Continued)

FOREIGN PATENT DOCUMENTS

| AU | 2002352871 | 9/2003 |
| AU | 2003261912 | 3/2004 |

(Continued)

OTHER PUBLICATIONS

International Search Report and Written Opinion from correspondence PCT Application No. PCT/IB2014/001121 dated Oct. 15, 2014, 11 pages.

(Continued)

*Primary Examiner* — Thomas J Sweet
*Assistant Examiner* — Seema Mathew
(74) *Attorney, Agent, or Firm* — Cadwalader Wickersham & Taft LLP

(57) ABSTRACT

An expandable helical stent with a securement is provided. The stent is formed from flat or tubular metal in a helical coiled structure which has an undulating pattern. The main stent component may be formed of a single helically coiled component. Alternatively, a plurality of helically coiled ribbons may be used to form a stent heterogeneous in design, material, or other characteristi. The helical tubular structure may be secured with a securement, such as a weld, interlock or a polymer, to maintain the helical coils in a tubular configuration. The helical coils of the main stent component may be spaced apart or nestled to each other. The nestling of the undulation of adjacent helical coils contributes to maintaining the tubular shape of the helically coiled stent. In addition, the nestling of helical coils may prevent the polymer layer from sagging at any point between cycles of the helical coils.

20 Claims, 15 Drawing Sheets

Related U.S. Application Data continuation-in-part of application No. 11/377,769, filed on Mar. 15, 2006, which is a continuation-in-part of application No. 11/331,639, filed on Jan. 13, 2006, which is a continuation-in-part of application No. 10/860,735, filed on Jun. 3, 2004, now abandoned, said application No. 11/377,769 is a continuation-in-part of application No. 10/607,604, filed on Jun. 27, 2003, now abandoned, application No. 13/829,153, which is a continuation-in-part of application No. 12/764,418, filed on Apr. 21, 2010.

(51) Int. Cl.
*A61L 31/02* (2006.01)
*A61L 31/10* (2006.01)
*A61F 2/91* (2013.01)
*A61L 31/14* (2006.01)
*A61F 2/90* (2013.01)
*A61F 2/915* (2013.01)
*A61F 2/82* (2013.01)

(52) U.S. Cl.
CPC .......... *A61F 2/915* (2013.01); *A61F 2002/825* (2013.01); *A61F 2002/91575* (2013.01); *A61L 31/146* (2013.01)

(56) References Cited

U.S. PATENT DOCUMENTS

| | | | |
|---|---|---|---|
| 4,142,571 A | | 3/1979 | Narasimhan |
| 4,144,058 A | | 3/1979 | Chen et al. |
| 4,185,383 A | | 1/1980 | Heimke et al. |
| 4,281,706 A | | 8/1981 | Liebermann et al. |
| 4,409,041 A | | 10/1983 | Datta et al. |
| 4,440,585 A | | 4/1984 | Kanehira |
| 4,473,401 A | | 9/1984 | Masumoto et al. |
| 4,481,001 A | | 11/1984 | Graham et al. |
| 4,489,773 A | | 12/1984 | Miller |
| 4,614,221 A | | 9/1986 | Masumoto |
| 4,655,771 A | | 4/1987 | Wallsten |
| 4,733,665 A | | 3/1988 | Palmaz |
| 4,755,593 A | | 7/1988 | Lauren |
| 4,760,849 A | | 8/1988 | Kropf |
| 4,762,128 A | | 8/1988 | Rosenbluth |
| 4,800,882 A | | 1/1989 | Gianturco |
| 4,802,776 A | | 2/1989 | Miyazawa et al. |
| 4,856,516 A | | 8/1989 | Hillstead |
| 4,886,062 A | | 12/1989 | Wiktor |
| 4,969,458 A | | 11/1990 | Wiktor |
| 5,019,090 A | | 5/1991 | Pinchuk |
| 5,037,377 A | | 8/1991 | Alonso |
| 5,045,637 A | | 9/1991 | Sato et al. |
| 5,102,417 A | | 4/1992 | Palmaz |
| 5,104,404 A | | 4/1992 | Wolff |
| 5,116,360 A | | 5/1992 | Pinchuk et al. |
| 5,116,365 A | | 5/1992 | Hillstead |
| 5,122,154 A | | 6/1992 | Rhodes |
| 5,123,917 A | | 6/1992 | Lee |
| 5,128,214 A | | 7/1992 | Takayanagi et al. |
| 5,133,732 A * | | 7/1992 | Wiktor .................. 623/1.22 |
| 5,161,547 A | | 11/1992 | Tower |
| 5,161,773 A | | 11/1992 | Tower |
| 5,195,984 A | | 3/1993 | Schatz |
| 5,282,824 A | | 2/1994 | Gianturco |
| 5,292,331 A | | 3/1994 | Boneau |
| 5,314,472 A * | | 5/1994 | Fontaine ............... 623/1.22 |
| 5,368,659 A | | 11/1994 | Peker et al. |
| 5,381,856 A | | 1/1995 | Fujikura et al. |
| 5,383,892 A | | 1/1995 | Cardon et al. |
| 5,393,594 A | | 2/1995 | Koyfman et al. |
| 5,405,377 A | | 4/1995 | Cragg |
| 5,421,919 A | | 6/1995 | Roman |
| 5,443,496 A | | 8/1995 | Schwartz et al. |
| 5,449,373 A | | 9/1995 | Pinchasik et al. |
| 5,464,438 A | | 11/1995 | Menaker |
| 5,510,077 A | | 4/1996 | Dinh et al. |
| 5,514,176 A | | 5/1996 | Bosley |
| 5,527,337 A | | 6/1996 | Stack et al. |
| 5,549,663 A * | | 8/1996 | Cottone, Jr. .................. 623/1.22 |
| 5,554,181 A | | 9/1996 | Das |
| 5,554,182 A | | 9/1996 | Dinh et al. |
| 5,556,413 A | | 9/1996 | Lam |
| 5,562,729 A | | 10/1996 | Purdy et al. |
| 5,571,166 A | | 11/1996 | Dinh et al. |
| 5,575,818 A | | 11/1996 | Pinchuk |
| 5,591,197 A | | 1/1997 | Orth et al. |
| 5,591,198 A * | | 1/1997 | Boyle et al. .................. 623/1.22 |
| 5,591,223 A | | 1/1997 | Lock et al. |
| 5,591,224 A | | 1/1997 | Schwartz et al. |
| 5,595,571 A | | 1/1997 | Jaffe et al. |
| 5,603,721 A | | 2/1997 | Lau et al. |
| 5,609,627 A | | 3/1997 | Goicoechea et al. |
| 5,618,299 A | | 4/1997 | Khosravi et al. |
| 5,626,604 A | | 5/1997 | Cottone |
| 5,628,785 A | | 5/1997 | Scwartz et al. |
| 5,632,771 A | | 5/1997 | Boatman et al. |
| 5,636,641 A | | 6/1997 | Fariabi |
| 5,653,747 A | | 8/1997 | Dereume |
| 5,672,169 A | | 9/1997 | Verbeek |
| 5,674,278 A | | 10/1997 | Boneau |
| 5,693,084 A | | 12/1997 | Chuter et al. |
| 5,693,085 A | | 12/1997 | Buirge et al. |
| 5,696,207 A | | 12/1997 | Vargo et al. |
| 5,716,396 A * | | 2/1998 | Williams, Jr. .................. 623/1.22 |
| 5,720,776 A | | 2/1998 | Chuter et al. |
| 5,720,777 A | | 2/1998 | Jaffe et al. |
| 5,723,003 A | | 3/1998 | Winston et al. |
| 5,725,573 A | | 3/1998 | Dearnaley et al. |
| 5,728,150 A | | 3/1998 | McDonald et al. |
| 5,733,303 A | | 3/1998 | Israel et al. |
| 5,755,781 A | | 5/1998 | Jayaraman |
| 5,769,884 A | | 6/1998 | Solovay |
| 5,779,732 A | | 7/1998 | Amundson |
| 5,782,905 A | | 7/1998 | Richter |
| 5,788,626 A | | 8/1998 | Thompson |
| 5,797,443 A | | 8/1998 | Lin et al. |
| 5,800,456 A * | | 9/1998 | Maeda et al. .................. 623/1.15 |
| 5,800,507 A | | 9/1998 | Scwartz et al. |
| 5,800,508 A | | 9/1998 | Goicoechea et al. |
| 5,800,509 A | | 9/1998 | Boneau |
| 5,807,404 A | | 9/1998 | Richter |
| 5,810,872 A * | | 9/1998 | Kanesaka et al. .................. 623/1.15 |
| 5,817,152 A | | 10/1998 | Birdsall et al. |
| 5,824,046 A | | 10/1998 | Smith et al. |
| 5,824,052 A | | 10/1998 | Khosravi et al. |
| 5,836,964 A | | 11/1998 | Richter et al. |
| 5,836,966 A | | 11/1998 | St. Germain |
| 5,843,120 A | | 12/1998 | Israel et al. |
| 5,843,180 A | | 12/1998 | Jaffe et al. |
| 5,843,181 A | | 12/1998 | Jaffe et al. |
| 5,849,034 A | | 12/1998 | Schwartz |
| 5,851,228 A | | 12/1998 | Pinheiro |
| 5,855,597 A | | 1/1999 | Jayaraman |
| 5,855,600 A | | 1/1999 | Alt |
| 5,865,723 A | | 2/1999 | Love |
| 5,879,381 A | | 3/1999 | Moriuchi et al. |
| 5,879,382 A | | 3/1999 | Boneau |
| 5,891,190 A | | 4/1999 | Boneau |
| 5,891,191 A | | 4/1999 | Stinson |
| 5,895,407 A | | 4/1999 | Jayaraman |
| 5,895,419 A | | 4/1999 | Tweden et al. |
| 5,899,934 A * | | 5/1999 | Amundson et al. .................. 623/1.11 |
| 5,902,332 A | | 5/1999 | Schatz |
| 5,913,895 A | | 6/1999 | Burpee et al. |
| 5,913,897 A * | | 6/1999 | Corso et al. .................. 623/1.15 |
| 5,922,020 A | | 7/1999 | Klein et al. |
| 5,922,021 A | | 7/1999 | Jang |
| 5,925,061 A * | | 7/1999 | Ogi et al. .................. 623/1.2 |
| 5,928,279 A | | 7/1999 | Shannon et al. |
| 5,931,867 A | | 8/1999 | Haindl |
| 5,938,697 A | | 8/1999 | Killion et al. |
| 5,955,145 A | | 9/1999 | Kalvala et al. |

(56) References Cited

U.S. PATENT DOCUMENTS

| | | |
|---|---|---|
| 5,964,770 A | 10/1999 | Flomenblit et al. |
| 5,997,973 A | 12/1999 | Bianca, Jr. |
| 6,013,091 A | 1/2000 | Ley et al. |
| 6,017,365 A | 1/2000 | Von Oepen |
| 6,027,525 A | 2/2000 | Suh et al. |
| 6,027,527 A | 2/2000 | Asano et al. |
| 6,042,605 A | 3/2000 | Martin et al. |
| 6,053,941 A | 4/2000 | Lindberg et al. |
| 6,059,808 A * | 5/2000 | Boussignac et al. .......... 606/191 |
| 6,080,192 A | 6/2000 | Demopulos et al. |
| 6,096,070 A | 8/2000 | Ragheb et al. |
| 6,120,534 A | 9/2000 | Ruiz |
| 6,120,847 A | 9/2000 | Yang et al. |
| 6,132,461 A | 10/2000 | Thompson |
| 6,139,573 A | 10/2000 | Sogard et al. |
| 6,159,237 A | 12/2000 | Alt et al. |
| 6,162,537 A | 12/2000 | Martin et al. |
| 6,179,868 B1 | 1/2001 | Burpee et al. |
| 6,183,353 B1 | 2/2001 | Frantzen |
| 6,187,034 B1 | 2/2001 | Frantzen |
| 6,187,095 B1 | 2/2001 | Labrecque et al. |
| 6,190,403 B1 | 2/2001 | Fischell et al. |
| 6,190,406 B1 | 2/2001 | Duerig et al. |
| 6,190,407 B1 | 2/2001 | Ogle et al. |
| 6,193,747 B1 | 2/2001 | Von Oepen |
| 6,197,048 B1 | 3/2001 | Richter |
| 6,221,098 B1 | 4/2001 | Wilson et al. |
| 6,224,625 B1 | 5/2001 | Javaraman |
| 6,231,598 B1 | 5/2001 | Berry et al. |
| 6,238,401 B1 | 5/2001 | Richter |
| 6,240,615 B1 | 6/2001 | Kimes et al. |
| 6,241,762 B1 | 6/2001 | Shanley |
| 6,251,059 B1 | 6/2001 | Apple et al. |
| 6,251,134 B1 | 6/2001 | Alt et al. |
| 6,258,116 B1 * | 7/2001 | Hojeibane .................... 623/1.16 |
| 6,258,117 B1 | 7/2001 | Camrud et al. |
| 6,264,689 B1 | 7/2001 | Colgan et al. |
| 6,273,910 B1 | 8/2001 | Limon |
| 6,287,333 B1 * | 9/2001 | Appling et al. .............. 623/1.22 |
| 6,299,604 B1 | 10/2001 | Ragheb et al. |
| 6,299,755 B1 | 10/2001 | Richter |
| 6,309,411 B1 | 10/2001 | Lashinski et al. |
| 6,312,459 B1 | 11/2001 | Huang et al. |
| 6,315,794 B1 | 11/2001 | Richter |
| 6,340,367 B1 | 1/2002 | Stinson et al. |
| 6,344,053 B1 | 2/2002 | Boneau |
| 6,348,065 B1 | 2/2002 | Brown et al. |
| 6,355,039 B1 * | 3/2002 | Troussel et al. ............... 606/264 |
| 6,355,059 B1 | 3/2002 | Richter |
| 6,383,213 B2 | 5/2002 | Wilson et al. |
| 6,387,120 B2 | 5/2002 | Wilson et al. |
| 6,398,803 B1 | 6/2002 | Layne |
| 6,409,753 B1 | 6/2002 | Brown et al. |
| 6,416,538 B1 | 7/2002 | Ley et al. |
| 6,428,569 B1 | 8/2002 | Brown |
| 6,440,162 B1 | 8/2002 | Cox et al. |
| 6,464,719 B2 | 10/2002 | Jayaraman |
| 6,471,980 B2 | 10/2002 | Sirhan et al. |
| 6,478,815 B1 | 11/2002 | Alt |
| 6,485,508 B1 | 11/2002 | McGuiness |
| 6,503,270 B1 * | 1/2003 | Richter et al. ............... 623/1.15 |
| 6,505,654 B1 | 1/2003 | Andersen et al. |
| 6,506,211 B1 | 1/2003 | Skubitz et al. |
| 6,506,408 B1 | 1/2003 | Palasis |
| 6,511,505 B2 | 1/2003 | Cox et al. |
| 6,527,801 B1 | 3/2003 | Dutta |
| 6,530,934 B1 | 3/2003 | Jacobsen et al. |
| 6,530,950 B1 | 3/2003 | Alvarado et al. |
| 6,540,774 B1 | 4/2003 | Cox |
| 6,540,775 B1 | 4/2003 | Fischell et al. |
| 6,558,414 B2 | 5/2003 | Layne |
| 6,562,065 B1 | 5/2003 | Shanley |
| 6,565,507 B2 | 5/2003 | Kamata et al. |
| 6,569,180 B1 | 5/2003 | Sirhan et al. |
| 6,579,310 B1 | 6/2003 | Cox et al. |
| 6,579,314 B1 | 6/2003 | Lombardi |
| 6,602,226 B1 | 8/2003 | Smith et al. |
| 6,602,281 B1 | 8/2003 | Klein |
| 6,602,282 B1 | 8/2003 | Yang et al. |
| 6,605,107 B1 | 8/2003 | Klein |
| 6,607,554 B2 | 8/2003 | Dang et al. |
| 6,610,086 B1 * | 8/2003 | Kock et al. .................... 623/1.22 |
| 6,638,301 B1 | 10/2003 | Chandrasekaran et al. |
| 6,645,240 B2 | 11/2003 | Yee |
| 6,648,911 B1 | 11/2003 | Sirhan et al. |
| 6,656,218 B1 | 12/2003 | Denardo et al. |
| 6,656,220 B1 | 12/2003 | Gomez et al. |
| 6,663,661 B2 | 12/2003 | Boneau |
| 6,673,106 B2 | 1/2004 | Mitelberg et al. |
| 6,699,278 B2 | 3/2004 | Fischell et al. |
| 6,706,061 B1 | 3/2004 | Fischell et al. |
| 6,709,453 B2 | 3/2004 | Pinchasik et al. |
| 6,723,119 B2 | 4/2004 | Pinchasik et al. |
| 6,730,117 B1 * | 5/2004 | Tseng et al. .................. 623/1.16 |
| 6,733,536 B1 | 5/2004 | Gellman |
| 6,736,844 B1 * | 5/2004 | Glatt et al. .................... 623/1.22 |
| 6,767,418 B1 | 7/2004 | Zhang et al. |
| 6,770,087 B2 | 8/2004 | Layne |
| 6,790,298 B2 | 9/2004 | Johnson et al. |
| 6,827,733 B2 | 12/2004 | Boneau |
| 6,863,757 B1 | 3/2005 | Gonzalez et al. |
| 6,866,805 B2 | 3/2005 | Hong et al. |
| 6,866,860 B2 | 3/2005 | Nathan |
| 6,899,727 B2 | 5/2005 | Armstrong et al. |
| 6,911,040 B2 | 6/2005 | Johnson |
| 6,962,604 B2 * | 11/2005 | Hijlkema ...................... 623/1.15 |
| 7,060,093 B2 | 6/2006 | Dang et al. |
| 7,108,714 B1 * | 9/2006 | Becker .......................... 623/1.15 |
| 7,112,293 B2 | 9/2006 | Dubson et al. |
| 7,176,344 B2 | 2/2007 | Gustafson et al. |
| 7,185,677 B2 * | 3/2007 | Houston et al. .................. 138/39 |
| 7,244,116 B2 | 7/2007 | Dubson et al. |
| 7,329,277 B2 * | 2/2008 | Addonizio et al. .......... 623/1.22 |
| 7,360,542 B2 | 4/2008 | Nelson et al. |
| 7,441,559 B2 | 10/2008 | Nelson et al. |
| 7,540,881 B2 * | 6/2009 | Meyer et al. ................. 623/1.35 |
| 7,637,939 B2 * | 12/2009 | Tischler ........................ 623/1.22 |
| 7,722,578 B2 | 5/2010 | Arney et al. |
| 7,722,661 B2 | 5/2010 | Lenz et al. |
| 7,887,584 B2 | 2/2011 | Richter |
| 7,901,448 B2 * | 3/2011 | Leopold et al. .............. 623/1.15 |
| 7,914,568 B2 * | 3/2011 | Cully et al. ................... 623/1.13 |
| 7,955,387 B2 | 6/2011 | Richter |
| 8,236,043 B2 * | 8/2012 | Caro et al. .................... 623/1.15 |
| 8,328,865 B2 * | 12/2012 | Bales et al. ................... 623/1.22 |
| 8,460,364 B2 * | 6/2013 | Cottone et al. ............... 623/1.22 |
| 8,496,703 B2 | 7/2013 | Richter |
| 2001/0020184 A1 | 9/2001 | Dehdashtian et al. |
| 2001/0032009 A1 | 10/2001 | Layne et al. |
| 2001/0056298 A1 | 12/2001 | Brown et al. |
| 2002/0004677 A1 | 1/2002 | Jayaraman |
| 2002/0007212 A1 | 1/2002 | Brown et al. |
| 2002/0046783 A1 | 4/2002 | Johnson et al. |
| 2002/0049488 A1 | 4/2002 | Boneau |
| 2002/0049489 A1 | 4/2002 | Herweck et al. |
| 2002/0049492 A1 | 4/2002 | Lashinski et al. |
| 2002/0052649 A1 | 5/2002 | Greenhalgh |
| 2002/0055770 A1 | 5/2002 | Doran et al. |
| 2002/0068969 A1 * | 6/2002 | Shanley et al. .............. 623/1.16 |
| 2002/0081732 A1 | 6/2002 | Bowlin et al. |
| 2002/0082680 A1 | 6/2002 | Shanley et al. |
| 2002/0082682 A1 | 6/2002 | Barclay et al. |
| 2002/0084178 A1 | 7/2002 | Dubson et al. |
| 2002/0103529 A1 | 8/2002 | Pinchasik et al. |
| 2002/0107560 A1 | 8/2002 | Richter |
| 2002/0116044 A1 * | 8/2002 | Cottone et al. ................. 623/1.2 |
| 2002/0116049 A1 | 8/2002 | Girton et al. |
| 2002/0120327 A1 | 8/2002 | Cox et al. |
| 2002/0138136 A1 | 9/2002 | Chandresekaran et al. |
| 2002/0161319 A1 | 10/2002 | Matsumoto et al. |
| 2002/0162605 A1 | 11/2002 | Horton, Jr. et al. |
| 2002/0165603 A1 | 11/2002 | Thornton et al. |
| 2002/0177893 A1 | 11/2002 | Brown et al. |
| 2003/0017208 A1 | 1/2003 | Ignatious et al. |

(56) References Cited

U.S. PATENT DOCUMENTS

| | | |
|---|---|---|
| 2003/0040803 A1 | 2/2003 | Rioux et al. |
| 2003/0045926 A1 | 3/2003 | Pinchasik |
| 2003/0050691 A1 | 3/2003 | Shifrin et al. |
| 2003/0069633 A1 | 4/2003 | Richter et al. |
| 2003/0083646 A1 | 5/2003 | Sirhan et al. |
| 2003/0120197 A1 | 6/2003 | Kaneko et al. |
| 2003/0130721 A1 | 7/2003 | Martin et al. |
| 2003/0208260 A1 | 11/2003 | Lau et al. |
| 2003/0211135 A1 | 11/2003 | Greenhalgh et al. |
| 2003/0212449 A1 | 11/2003 | Cox |
| 2004/0044401 A1* | 3/2004 | Bales et al. ............... 623/1.22 |
| 2004/0064180 A1 | 4/2004 | Boneau |
| 2004/0072124 A1 | 4/2004 | Kaufman et al. |
| 2004/0082989 A1 | 4/2004 | Cook et al. |
| 2004/0088043 A1 | 5/2004 | Klein |
| 2004/0098095 A1 | 5/2004 | Burnside |
| 2004/0102833 A1 | 5/2004 | Girton et al. |
| 2004/0106980 A1 | 6/2004 | Solovay et al. |
| 2004/0193251 A1* | 9/2004 | Rudnick et al. .............. 623/1.22 |
| 2004/0199242 A1 | 10/2004 | Hong et al. |
| 2004/0230291 A1 | 11/2004 | Richter |
| 2004/0236402 A1 | 11/2004 | Layne |
| 2004/0254419 A1 | 12/2004 | Wang et al. |
| 2004/0255096 A1 | 12/2004 | Norman |
| 2004/0267349 A1 | 12/2004 | Richter |
| 2005/0033399 A1* | 2/2005 | Richter ........................ 623/1.11 |
| 2005/0084407 A1 | 4/2005 | Myrick |
| 2005/0107864 A1 | 5/2005 | Hong et al. |
| 2005/0113888 A1 | 5/2005 | Jimenez et al. |
| 2005/0131515 A1* | 6/2005 | Cully et al. .................. 623/1.13 |
| 2005/0209679 A1 | 9/2005 | Melsheimer |
| 2005/0216076 A1* | 9/2005 | Kveen et al. ................. 623/1.22 |
| 2005/0246010 A1* | 11/2005 | Alexander et al. ........... 623/1.12 |
| 2005/0261758 A1 | 11/2005 | Rourke et al. |
| 2005/0278019 A1* | 12/2005 | Gregorich .................... 623/1.44 |
| 2006/0030934 A1* | 2/2006 | Hogendijk et al. ........... 623/1.22 |
| 2006/0122691 A1 | 6/2006 | Richter |
| 2006/0149386 A1 | 7/2006 | Clarke et al. |
| 2006/0178727 A1 | 8/2006 | Richter |
| 2006/0246210 A1 | 11/2006 | Iki et al. |
| 2007/0073383 A1 | 3/2007 | Yip et al. |
| 2007/0150046 A1 | 6/2007 | Meyer et al. |
| 2007/0208409 A1 | 9/2007 | Quigley |
| 2007/0219618 A1* | 9/2007 | Cully et al. .................. 623/1.13 |
| 2007/0239264 A1* | 10/2007 | Fliedner ....................... 623/1.16 |
| 2007/0250148 A1* | 10/2007 | Perry et al. .................. 623/1.11 |
| 2007/0269936 A1 | 11/2007 | Tanaka et al. |
| 2008/0097582 A1* | 4/2008 | Shanley et al. .............. 623/1.22 |
| 2008/0215129 A1 | 9/2008 | Venturelli et al. |
| 2008/0221664 A1* | 9/2008 | Bales et al. .................. 623/1.22 |
| 2008/0319534 A1 | 12/2008 | Birdsall et al. |
| 2008/0319535 A1 | 12/2008 | Craven et al. |
| 2009/0012525 A1 | 1/2009 | Buehlmann et al. |
| 2009/0036976 A1* | 2/2009 | Beach et al. ................. 623/1.22 |
| 2009/0062903 A1 | 3/2009 | Pathak |
| 2009/0210049 A1 | 8/2009 | Thielen et al. |
| 2009/0234433 A1* | 9/2009 | Richter ........................ 623/1.17 |
| 2009/0259294 A1 | 10/2009 | Cully et al. |
| 2009/0264986 A1 | 10/2009 | Bales et al. |
| 2009/0306766 A1* | 12/2009 | McDermott et al. ......... 623/1.16 |
| 2010/0004725 A1* | 1/2010 | Zipse et al. .................... 623/1.2 |
| 2010/0070024 A1* | 3/2010 | Venturelli et al. ............ 623/1.22 |
| 2010/0198333 A1* | 8/2010 | Macatangay et al. ........ 623/1.15 |
| 2011/0004290 A1* | 1/2011 | Bales et al. .................. 623/1.16 |
| 2011/0125251 A1* | 5/2011 | Cottone et al. ............... 623/1.16 |
| 2011/0184507 A1* | 7/2011 | Fischer, Jr. et al. ......... 623/1.16 |
| 2011/0218615 A1* | 9/2011 | Griswold ...................... 623/1.15 |
| 2011/0251668 A1 | 10/2011 | Thompson et al. |
| 2012/0265288 A1* | 10/2012 | Jones et al. .................. 623/1.11 |
| 2012/0303112 A1* | 11/2012 | Armstrong et al. .......... 623/1.16 |
| 2013/0090721 A1* | 4/2013 | Bales et al. .................. 623/1.22 |
| 2014/0135904 A1* | 5/2014 | Rowe ............................ 623/1.22 |
| 2014/0379066 A1* | 12/2014 | Burpee et al. ................ 623/1.11 |

FOREIGN PATENT DOCUMENTS

| | | |
|---|---|---|
| CA | 2092337 | 9/1993 |
| CA | 2281775 | 6/2000 |
| CA | 2370184 | 10/2000 |
| DE | 195 12 066 | 11/1996 |
| DE | 297 08 879 | 9/1997 |
| DE | 197 53 123 | 8/1999 |
| DE | 199 00 411 | 7/2000 |
| DE | 199 57 063 | 8/2001 |
| DE | 102 23 399 | 6/2006 |
| EP | 0 364 787 A1 | 4/1990 |
| EP | 0 623 354 | 11/1994 |
| EP | 0 747 498 A2 | 12/1996 |
| EP | 0 775 472 A2 | 5/1997 |
| EP | 0 334 046 B1 | 6/1997 |
| EP | 0 830 853 | 3/1998 |
| EP | 0 888 757 | 1/1999 |
| EP | 0 916 318 | 5/1999 |
| EP | 0 958 794 | 12/1999 |
| EP | 0 970 664 | 1/2000 |
| EP | 0 876 216 | 4/2000 |
| EP | 1 020 166 | 7/2000 |
| EP | 1 129 673 | 9/2001 |
| EP | 1 216 717 A1 | 6/2002 |
| EP | 1 148 843 | 4/2003 |
| EP | 1 477 130 | 11/2004 |
| EP | 1 834 606 | 9/2007 |
| EP | 1 997 459 | 12/2008 |
| EP | 1 937 184 B1 | 2/2010 |
| EP | 2 526 905 A1 | 11/2012 |
| EP | 2 529 706 A1 | 12/2012 |
| FR | 2 758 253 | 7/1998 |
| JP | 61-106133 | 5/1986 |
| JP | 01-121064 | 5/1989 |
| JP | 02-047243 | 2/1990 |
| JP | 02-057264 | 2/1990 |
| JP | 2061036 A | 3/1990 |
| JP | 2-174859 | 7/1990 |
| JP | 03-009746 | 1/1991 |
| JP | 07-080078 | 3/1995 |
| JP | 07-124263 | 5/1995 |
| JP | 07-188876 | 7/1995 |
| JP | 07-265432 | 10/1995 |
| JP | 08-243107 | 9/1996 |
| JP | 10-277082 | 10/1998 |
| JP | 2000-167064 | 6/2000 |
| JP | 2000-000297 | 7/2000 |
| JP | 2001-231867 | 8/2001 |
| JP | 2004-089580 | 3/2004 |
| JP | 2005-522594 | 7/2005 |
| JP | 2007-527734 | 10/2007 |
| NZ | 280547 | 9/1998 |
| NZ | 285241 | 3/1999 |
| NZ | 331532 | 1/2000 |
| WO | WO 83/00997 | 3/1983 |
| WO | WO 93/13825 | 7/1993 |
| WO | WO 95/03010 | 2/1995 |
| WO | WO 95/23876 | 9/1995 |
| WO | WO 95/26695 | 10/1995 |
| WO | WO 96/26689 | 9/1996 |
| WO | WO 97/07889 | 3/1997 |
| WO | WO 97/25937 | 7/1997 |
| WO | WO 97/32544 | 9/1997 |
| WO | WO 97/33534 | 9/1997 |
| WO | WO 97/37617 | 10/1997 |
| WO | WO 98/22159 | 5/1998 |
| WO | WO 98/35634 | 8/1998 |
| WO | WO 98/41169 | 9/1998 |
| WO | WO 99/15108 | 4/1999 |
| WO | WO 99/17680 | 4/1999 |
| WO | WO 99/33410 | 7/1999 |
| WO | WO 99/39660 | 8/1999 |
| WO | WO 99/44543 | 9/1999 |
| WO | WO 99/62431 | 12/1999 |
| WO | WO 00/30563 | 6/2000 |
| WO | WO 00/32138 | 6/2000 |
| WO | WO 00/49971 | 8/2000 |
| WO | WO 01/52771 | 7/2001 |

(56) References Cited

FOREIGN PATENT DOCUMENTS

| WO | WO 01/58504 | 8/2001 |
|---|---|---|
| WO | WO 02/26279 A1 | 4/2002 |
| WO | WO 02/35984 | 5/2002 |
| WO | WO 03/057075 | 7/2003 |
| WO | WO 03/057077 | 7/2003 |
| WO | WO 03/082152 | 10/2003 |
| WO | WO 03/087443 | 10/2003 |
| WO | WO 2004/016197 | 2/2004 |
| WO | WO 2004/045454 A | 6/2004 |
| WO | WO 2005/000152 | 1/2005 |
| WO | WO 2005/034806 A1 | 4/2005 |
| WO | WO 2005/058202 | 6/2005 |
| WO | WO 2005/070337 | 8/2005 |
| WO | WO 2005/072653 | 8/2005 |
| WO | WO 2005/102220 | 11/2005 |
| WO | WO 2005/118971 | 12/2005 |
| WO | WO 2006/014969 | 2/2006 |
| WO | WO 2006/086069 A2 | 8/2006 |
| WO | WO 2007/105088 | 9/2007 |
| WO | WO 2008/049045 | 4/2008 |
| WO | WO 2008/100783 | 8/2008 |

OTHER PUBLICATIONS

European Search Report dated Dec. 2, 2003, 5 pages from related abandoned Application No. 01125340.8.
European Search Report dated Oct. 25, 2004, 5 pages from related abandoned Application No. 01125341.6.
European Search Report dated Mar. 11, 2005, 4 pages from related abandoned Application No. 02733008.3.
Supplemental European Search Report dated Sep. 5, 2007, 3 pages from related Application No. EP 04737140.
Supplemental European Search Report dated Aug. 31, 2009, 3 pages from related Application No. EP 07700481.
Extended EP Search Report, Application No. EP 09008421.1 dated Jan. 15, 2010.
Extended EP Search Report, Application No. EP09008420.3 dated Jan. 15, 2010.
Extended EP Search Report, Application No. EP 09008419.5 dated Jan. 15, 2010.
Extended EP Search Report, Application No. EP07733978.6 dated Mar. 17, 2010.
Extended European Search Report dated Jul. 7, 2010 for EP Application No. 10004585.5-1219, 7 pages.
EP Search Report dated Jul. 3, 2008, Application No. EP 1751363.
Extended EP Search Report, Publ No. EP 1996113 / App. No. EP 07733978.6dated Mar. 17, 2010.
International Search Report and Written Opinion dated Aug. 4, 2010 for PCT Application No. PCT/IB2010/001036, 13 pages.
PCT International Search Report, Application No. PCT/US98/19990 dated May 6, 1999.
PCT International Search Report and Written Opinion dated Apr. 5, 2005, 10 pages from related PCT Application No. PCT/IB04/02096.
PCT International Search Report dated May 9, 2009, Application No. PCT/IB05/01524 / Published No. WO 05/118971.
PCT International Search Report and Written Opinion dated Jun. 11, 2008, 9 pages from related Application No. PCT/IB2007/000088.
PCT International Search Report, Dec. 8, 2008, 7 pages, from co-pending PCT Application No. PCT/IB2007/000632.
International Preliminary Report on Patentability dated Feb. 25, 2010, 8 pages from related Application No. PCT/IB2008/002515.
PCT International Search Report and Written Opinion dated Dec. 3, 2009, 14 pages from related Application No. PCT/IB2008/002515.
GB Search Report under Section 17 of the 1977 Patent Act dated Apr. 8, 2004, 1 pages from related Application No. GB 0402845.2.
Translation of an OA issued by the German Patent and Trademark Office dated Feb. 28, 2008, Application No. DE 19956249.0-43.
Singapore Search and Examination Report dated Sep. 13, 2000, Application No. 9904228-8.
New Zealand Examination Report dated Sep. 8, 1999, Application No. 337652.
BSC Cancellation Proceeding v. Medinol DE 20108764, NIRflex dated Jan. 11, 2005.
BSC Cancellation Proceeding v. Medinol DE 20108765, NIRflex dated Jan. 11, 2005.
Horton et al., "Biomedical Potential of a Zirconium-Based Bulk Metallic Glass" Mat. Res. Soc. Symp. Proc. vol. 754, Materials Research Society, Feb. 14, 2003, http://www.ornl.gov/webworks/cppr/y2001/pres/116372.pdf.
Database WPI Week 20012 Derwent Publications Ltd., London GB; AN 2000-129595 XP002446760 / JP 20000-000297 A (Inoue A) Jan. 7, 2000.
Busch, R. et al., "On the Glass Forming Ability of Bulk Metallic Glass", Materials Science Forum vols. 235-238 (1997) pp. 327-336.
Cahn, R., "Atomic Transport in Amorphous Alloys: An Introduction", J.Vac. Sci, Technol. A (4(6), Nov./Dec. 1986.
Donaldson, J., "Metallic Glasses: A New Class of Electroplated Coatings", Surface Finishing, Jul. 1986.
Duwez, P. "A Typical Example of Metastability: Metallic Glasses", J.Vac. Sci. Technol. B1 (2) Apr.-Jun. 1983.
Fecht, H. et al., "Destabilization and Vitrification of Crystalline Matter", J. Non-Crystalline Solids, 117/118 (1990) 704-707.
Johnson, W.L. et al., "Electronic Structure of Metallic Glasses", Glassy Metals: Magnetic, Chemical, and Structural Properties, CRC press, pp. 65-108.
Johnson, W.L., "Fundamental Aspects of Bulk Metallic Glass formation in Multicomponent Assays", Materials Science Forum, vols. 225-227 (1996) pp. 35-50.
Johnson, W.L., "Bulk Metallic Glasses—A New Engineering Material", current Opinion in Solid State & Materials Science, 1996, 1:383-386.
Johnson, W.L., "Mechanisms of Instability in Crystalline Alloys with Respect to Vitrification", Journal of Less-Common Metals, 145 (1988) 63-80.
Kavesh, S., "Principles of Fabrication", Metallic Glasses, Papers presented at a Seminar of the Materials Science Division of the American Society for Metals, Sep. 18 and 19, 1976.
Kukulka, D., "New Chill-block Melt Spinning Relations to Predict Ribbon Thickness", J. Thermophysics, vol. 10, No. 3, Technical Notes, 1996.
Kung, K. T-Y., "Electrical Characteristics of Amorphous Molybdenum-Nickel Contacts to Silicon", J.Appl. Phys., 55(10), May 15, 1984 pp. 3882-3885.
Liebermann, H., et al., "Technology of Amorphous Alloys", ChemTech, Jun. 1987, pp. 363-367.
Liebermann, H.H., "The Dependence of the Geometry of Glassy Alloy Ribbons on the Chill Bock Melt-Spinning Process Parameters", Materials Science and Engineering, 43 (1980) 203-210.
Takayama, S., et al., "The Analysis of Casting Conditions of Amorphous Alloys", J. Appl. Phys. 50 (7), Jul. 1979, pp. 4962-4965.
Thakoor, A.P. et al., "Influence of the Microstructure on the Corrosion Behavior of Magnetron Sputter-Quenched Amorphous Metal Alloys", J. Vac. Sci. Technol. A 1 (2), Apr.-Jun. 1983, pp. 520-523.
Williams, R.M. et al., "Corrosion Behavior of Magnetron Sputter-Deposited [$Mo_{0.6}Ru_{0.4}$]$B_{18}$ and $Mo_{82}B_{18}$ Amorphous Metal Films", J. Electrochemical Soc., vol. 131 No. 12, pp. 2791-2794.
Zhu, M.F. et al., "Electrical Characteristics of Amorphous $Ni_{36}W_{64}$ Contacts on SI", Advanced Semiconductor Processing and Characterization of Electronic and Optical Materials, Proceedings of SPIE, vol. 463, Jan. 24-25, 1984.
Zhu, M. F., et al., "Investigation of Amorphous $W_{60}Zr_{40}$ Film as a Diffusion Barrier in Metallization Schemes", Phys. Stat. Sol. (a) S6, 471 (1984).
"Technology: Hot Alloy" [online]. Forbes Magazine, Sep. 30, 2002[retrieved Feb. 19, 2003] Retrieved from the internet: <URL:www.forbes.com/global/2002/0930/128.html>.
"Innovative Material is Stronger than Titanium but can be formed like a Plastic" [online]. Jobwerx Manufacturing Network. [retrieved Feb. 19, 2003]. Retrieved from the internet: <URL:www.jobwerx.com/news/archives/LiquidmetalAlloys.com>.
"Liquidmetal Medical Devices" [online], Liquidmetal Technologies, [retrieved Feb. 20, 2003]. Retrieved from the internet: <URL:www.liquidmetal.com/applications/dsp.medical.asp>.

(56) References Cited

OTHER PUBLICATIONS

"Liquidmetal Technology Reborn in LMG" [online]. Golfweb, Jul. 31, 2002 [retrieved Feb. 20, 2003]. Retrieved from the internet: <URL:www.golfweb.com/u/cd/multi/0,1977m5564401,00.html>.

"Choosing the right suture material" [online], The Royal College of Surgeons of Edinburgh [retrieved Mar. 5, 2003]. Retrieved from the internet <URL: www.edu.rcsed.ac.uk/lectures/lt5.htm>.

"BBC health—Ask the Doctor—Heart Valves Replacement" [online]. BBC health homepage, Jul. 18, 2001. [retrieved Mar. 12, 2003]. Retrieved from the internet: <URL: www.bbc.co.uk/health/ask_doctor/heartvalve_replacement.shtml>.

"Artificial Organs Cardiovascular" [online]. National University of Singapore. [retrieved Feb. 12, 2003]. Retrieved from the internet <URL: www.scholars.nus.edu.sg/cpace/prosthesis/stein/cardio.html>.

"Heart replacement valves" [online]. Research Defense Society. [retrieved Mar. 12, 2003]. Retrieved from the internet: <URL: www.rds-online.org.uk/milestones/valves.html>.

"Material considerations in Replacement Heart Valves" [online]. Rose-Hulman Institute of Technology Fall 1996 [retrieved Mar. 12, 2003]. Retrieved from the internet: <URL: www.rose-hulman.edu/class/scheme/HTML/SiteMap/Undergraduate/StudentProjects/MaterialsStudentProjects/heart/heart.html>.

"The Physics Behind Artificial Heart Valves" [online]. Claire Carson, et al., Dec. 4, 2000 [retrieved Mar. 12, 2003] Retrieved from the internet: <URL: www.ipass.net/~tonyg/HeartValvesWeb.html>.

"Medical Dictionary—Artificial Heart Valve" [online]. Dr. Malcolm C. Brown, 2000 [retrieved on Mar. 12, 2003]. Retrieved from the internet: <URL: http://www.thebrowns23.freeserve.co.uk/entries/ARTIFICIAL_HEART_VALVE>.

Jostent Peripheral Stent Graft [online]. JOMED 2002, [retrieved Mar. 14, 2003]. Retrieved from the internet: <URL:www.jomed.com/products/jpsg/productinfo/jostent-psg.html>.

"Recent Advances in Titanium Wire Technology", [online]. TP Orthodontics, Inc. Jan. 1999 [retrieved Mar. 15, 2003]. Retrieved from the internet: <URL:http://www.tportho.com/doctorsroom/whitepapers/pdf/titanium.pdf>.

"Dental Implants" [online]. Niagara Oral Surgery [retrieved on Mar. 17, 2003] <URL: www.niagaraoralsurgery.com/ser_implants.htm>.

"Lecture 11—Metals for Implantation", [online]. Wayne State University, [retrieved Mar. 17, 2003]. Retrieved from the internet: <URL:http://ttb.eng.wayne.edu/~grimm/BME5370/Lect11Out.html>.

"Investment Materials" [online]. Guy's, King's College & St. Thomas's Hospital Dental Institute, Dental Biomaterials Science, R.V. Curtis [retrieved Mar. 15, 2003]. Retrieved from the internet: <URL: http://r-curtis.umds.ac.uk/bds3a/investment%20materials%201.htm>.

"Metal Casting Alloys" [online]. Guy's, King's College & St. Thomas's Hospital Dental Institute, Dental Biomaterials Science, R.V. Curtis [retrieved on Mar. 15, 2003]. Retrieved from the internet: <URL: http://r-curtis.umds.ac.uk/bds3a/BMCalloys.HTM>.

"Metals & Alloys" [online]. Guy's, King's College & St. Thomas's Hospital Dental Institute, Dental Biomaterials Science, R.V. Curtis, [retrieved on Mar. 15, 2003]. Retrieved from the internet: <URL: http://r-curtis.umds.ac.uk/bds3a/metallurgy.HTM>.

"TP Original Wire: Development of a High-Performance Orthodontic Wire", [online]. TP Orthodontics, Inc. 1998 [retrieved on Mar. 15, 2003]. Retrieved from the internet: <URL: http://www.tportho.com.br/doctorsroom/whitepapers/pdf/originalwire.pdf>.

"Metallic Glasses Bulk Up", [online]. Mechanical Engineering Magazine, Jun. 1998. [retrieved on Mar. 21, 2003]. Retrieved from the internet: <URL:www.memagazine.org/backissues/june98/features/metallic/metallic.html>.

"Hasta La Vista, Titanium", [online]. Business 2.0, Oct. 2002. [retrieved on Mar. 21, 2003]. Retrieved from the internet: <URL:www.business2.com/articles/mag/print/0,1643,43538,00.html>.

"New metal alloy is super strong", [online]. You magazine. [retrieved on Mar. 21, 2003]. Retrieved on the internet: <URL:www.yo.com.au/news/1022.htm>.

"Lessons of the Björk-Shiley Heart Valve Failure, Mechanics of Heart Valves" [online]. University of Texas at Austin. [retrieved on Mar. 25, 2003]. retrieved from the internet: <URL: www.me.utexas.edu/~uer/heartvalves/mechanics.html>.

Atzmon, M. et al., "Study of Amorphouse Phases Formed by Solid-State Reaction in Elemental Composites", Rapidly Quenched Metals, Proceedings of the Fifth International Conference on Rapidly Quenced Metals, Wüzburg, Germany, Sep. 3-7, 1984.

Office Actions and Responses to Office Actions of related co-pending U.S. Appl. No. 11/377,769, filed Mar. 15, 2006: Request for Continued Examination and Response to Final Rejection dated Apr. 13, 2012; Final Rejection dated Jan. 13, 2012; Amendment and Response to Non-Final Rejection dated Nov. 30, 2011; Non-Final Rejection dated Aug. 1, 2011; Amendment and Response to Final Rejection with Request for Continued Examination dated Sep. 15, 2010; Final Rejection dated Jun. 15, 2010; Amendment and Response to Non-Final Rejection dated Mar. 24, 2010; Non-Final Rejection dated Dec. 24, 2009; Amendment and Response to Restriction Requirement Sep. 28, 2009; and Requirement for Restriction/Election dated Aug. 27, 2009.

Office Actions and Responses to Office Actions of related co-pending U.S. Appl. No. 12/428,347, filed Apr. 22, 2009: Issue Notification dated Feb. 6, 2013; Applicant Initiated Interview Summary dated Jan. 29, 2013; Response to Amendment under Rule 312; Notice of Allowance dated Oct. 2, 2012; Supplemental Response to Non-Final Rejection dated May 9, 2012; Amendment and Response to Non-Final Rejection dated Mar. 22, 2012; Non-Final Rejection dated Dec. 23, 2011; Examiner Interview Summary dated Jul. 21, 2011; and Non-Final Rejection dated Apr. 27, 2011.

Office Actions and Responses to Office Actions of related abandoned U.S. Appl. No. 10/860,735, filed Jun. 3, 2004: Notice of Abandonment dated Jun. 6, 2007; Examiner Interview Summary Record dated Apr. 4, 2007; Non-Final Rejection dated Oct. 11, 2006; Response to Election/Restriction Requirement with Extension of Time dated Aug. 11, 2006; and Requirement for Restriction/Election dated Apr. 11, 2006.

Office Actions and Responses to Office Actions of related co-pending U.S. Appl. No. 11/331,639, filed Jan. 13, 2006: Request for Continued Examination, Amendment and Response to Final Rejection with Extension dated Jan. 16, 2014; Final Rejection dated Sep. 27, 2013; Amendment and Response to Non-Final Rejection dated Sep. 12, 2013; Non-Final Rejection dated Jun. 26, 2013; Amendment and Response to Final Rejection with Request for Continued Examination dated Aug. 4, 2010; Examiner Interview Summary dated Jun. 29, 2010; Final Rejection dated May 4, 2010; and Amendment and Response to Non-Final Rejection with Extension of Time dated Feb. 2, 2010; Non-Final Rejection dated Sep. 2, 2009; Request for Continued Examination, Amendment after Final Office Action, and Extension dated Jun. 18, 2009; Advisory Action dated Jun. 17, 2009; Amendment after Final Office Action dated May 18, 2009; Final Rejection dated Feb. 18, 2009; Applicant Summary of Interview with Examiner dated Jan. 12, 2009; Examiner Interview Summary Records dated Dec. 5, 2008; Response to Election/Restriction Requirement dated Dec. 1, 2008; Requirement for Restriction/Election dated Oct. 31, 2008; Replacement Drawings under 37 CFR 1.121(d) filed Aug. 1, 2008; Examiner Interview Summary dated Jul. 29, 2008; Amendment and Response to Non-Final Rejection with Extension dated Jul. 28, 2008; and Non-Final Rejection dated Jun. 30, 2008.

Office Actions and Responses to Office Actions of related co-pending U.S. Appl. No. 11/729,516, filed Mar. 28, 2007: Advisory Action dated Oct. 31, 2014; Amendment and Response to Final Rejection dated Oct. 22, 2014; Final Rejection dated Aug. 22, 2014; Amendment and Response to Non-Final Rejection with Extension dated Aug. 1, 2014; Non-Final Rejection dated Apr. 9, 2014; Applicant Initiated Interview Summary dated May 4, 2012; Request for Continued Examination, Amendment and Response to Final Rejection dated May 1, 2012; Final Rejection dated Feb. 1, 2012; Amendment and Response to Non-Final Rejection dated Dec. 20, 2011; and Non-Final Rejection dated Sep. 20, 2011; Request for Continued

(56) References Cited

OTHER PUBLICATIONS

Examination, Amendment and Response to Final Rejection dated Apr. 6, 2011; Final Rejection dated Jan. 7, 2014; Amendment and Response to Non-Final Rejection dated Nov. 8, 2010; and Non-Final Rejection dated Aug. 6, 2010.

Office Actions and Responses to Office Actions of related co-pending U.S. Appl. No. 10/607,604, filed Jun. 27, 2003: Notice of Abandonment dated Jun. 4, 2009; Final Rejection dated Dec. 3, 2008; Amendment and Response to Non-Final Rejection with Extension of Time dated Nov. 13, 2007; Non-Final Rejection dated Jul. 12, 2007; Amendment and Response to Final Rejection with Request for Continued Examination & Extension of Time dated May 2, 2007; Final Rejection dated Nov. 6, 2006; Amendment and Response to Non-Final Rejection with Extension of Time dated Aug. 11, 2006; Non-Final Rejection dated May 1, 2006; Request for Continued Examination & Extension of Time dated Apr. 7, 2006; Advisory Action dated Mar. 31, 2006; Amendment and Response to Final Rejection dated Mar. 13, 2006; Final Rejection date Dec. 12, 2005; Amendment and Response to Notice of Non-Compliance dated Sep. 15, 2005; Notice of Non-Compliant or Non-Responsive Amendment dated Aug. 24, 2005; Amendment and Response to Non-Final Rejection dated May 18, 2005; Non-Final Rejection dated Feb. 23, 2005; Response to Restriction Requirement dated Dec. 17, 2004; and Requirement for Restriction/Election dated Nov. 17, 2004.

Office Actions and Responses to Office Actions of related co-pending U.S. Appl. No. 12/243,723, filed Oct. 1, 2008: Notice of Allowances dated Nov. 24, 2010, Oct. 29, 2010 and Oct. 5, 2010; Amendment and Response to Final Rejection with Request for Continued Examination dated Jul. 7, 2010; Examiner Interview Summary Record dated Jun. 29, 2010; Final Rejection dated Apr. 7, 2010; Amendment and Response to Non-Final Rejection dated Dec. 18, 2009; and Non-Final Rejection dated Sep. 18, 2009.

Office Actions and Responses to Office Actions of related co-pending U.S. Appl. No. 12/243,732, filed Oct. 1, 2008: Notice of Abandonment dated Oct. 28, 2010; Examiner Interview Summary Record dated Jun. 29, 2010; Final Rejection dated Apr. 9, 2010; Amendment and Response to Non-Final Rejection with Extension of Time dated Jan. 20, 2010; and Non-Final Rejection dated Sep. 21, 2009.

Office Actions and Responses to Office Actions of related U.S. Appl. No. 12/243,741, filed Oct. 1, 2008: Supplemental Notice of Allowability dated May 9, 2011; Supplemental Notice of Allowability dated Apr. 29, 2011; Applicant Summary of Interview with Examiner dated Feb. 28, 2011; Notice of Allowance and Fees Due w/ Examiner Interview Summary Recorded dated Jan. 28, 2011; Amendment and Response to Non-Final Rejection dated Nov. 29, 2010; and Non-Final Rejection dated Sep. 30, 2010.

Office Actions and Responses to Office Actions of related abandoned U.S. Appl. No. 09/204,830, filed Dec. 3, 1998: Notice of Abandonment dated Oct. 1, 2002; Request for Extension of Time dated Apr. 5, 2002; Final Rejection dated Dec. 11, 2001; Amendment and Response after Non-Final Rejection dated Oct. 10, 2001; Non-Final Rejection dated Sep. 10, 2001; Request for Continued Examination dated Jul. 27, 2001; Advisory Action dated Jul. 18, 2001; Amendment and Response after Final Rejection dated Jul. 11, 2001; Final Rejection dated May 11, 2001; Amendment and Response after Non-Final Rejection with Extension of Time dated Mar. 7, 2001; Non-Final Rejection dated Sep. 18, 2000; Continuing Prosecution Application dated Aug. 16, 2000; Advisory Action dated Jul. 31, 2000; Amendment after Final Rejection dated Jul. 3, 2000; Final Rejection dated May 5, 2000; Response after Non-Final Rejection dated Jan. 31, 2000; and Non-Final Rejection dated Aug. 3, 1999.

Office Actions and Responses to Office Actions of related abandoned U.S. Appl. No. 10/116,159, filed Apr. 5, 2002: Notice of Abandonment dated Jan. 25, 2005; Advisory Action dated Jul. 20, 2004; Amendment and Response after Final Rejection dated Jun. 30, 2004; Final Rejection dated Jun. 8, 2004; Amendment and Response after Non-Final Rejection dated Mar. 24, 2004; Non-Final Rejection dated Dec. 1, 2003; Response to Restriction/Election Requirement dated Sep. 17, 2003; and Requirement for Restriction/Election dated Aug. 26, 2003.

Extended EP Search Report dated Oct. 1, 2012 for EP Appl. No. 12181899.1-2320 / EP 12181899.

Extended EP Search Report dated Nov. 15, 2012 or EP 12187494.5-2320.

Office Actions and Response to Office Actions of related U.S. Appl. No. 12/764,418, filed Apr. 21, 2010: Amendment and Response to Non-Final Rejection with Extension due Oct. 10, 2014; Non-Final Rejection dated Jun. 10, 2014; Request for Continued Examination, Amendment and Response to Final Rejection dated Oct. 8, 2013; Final Rejection dated Jul. 8, 2013; Amendment and Response to Non-Final Rejection dated Feb. 27, 2013; Applicant Initiated Interview Summary dated Feb. 14, 2013; Non-Final Rejection dated Nov. 28, 2012; Preliminary Amendment dated Jul. 23, 2012; Response to Election/Restriction requirement dated Jan. 27, 2012; and Requirement for Restriction/Election dated Dec. 28, 2011.

Office Actions and Responses to Office Actions of related U.S. Appl. No. 13/467,800, filed May 9, 2012: Non-Final Rejection, Examiner Initiated Interview Summary and Letter Restarting Period for Response dated Nov. 10, 2014; Non-Final Rejection dated Aug. 27, 2014; Response to Election/Restriction requirement dated Jul. 1, 2014; and Requirement for Response/Restriction dated May 6, 2014.

Office Actions and Responses to Office Actions of related U.S. Appl. No. 13/786,631, filed Mar. 6, 2013: Non-Final Rejection dated Nov. 5, 2014; Response to Election/Restriction Requirement dated Jul. 1, 2014; Requirement for Restriction/Election dated May 7, 2014.

Office Actions and Responses to Office Actions of related U.S. Appl. No. 13/596,671, filed Aug. 28, 2012: Request for Continued Examination, Extension and Response to Final Rejection dated Sep. 15, 2014; Advisory Action dated Jul. 24, 2014; Response to Final Rejection dated Jul. 17, 2014; Final Rejection dated Apr. 18, 2014; Amendment and Response to Non-Final Rejection dated Dec. 16, 2013; and Non-Final Rejection dated Sep. 16, 2013.

Office Actions and Responses to Office Actions of related U.S. Appl. No. 13/096,561, filed Aug. 28, 2011: Notice of Allowance and Applicant Initiated Interview Summary dated May 29, 2013; Advisory Action dated May 7, 2013; Response to Final Rejection dated Apr. 11, 2013; Final Rejection dated Feb. 11, 2013; Terminal Disclaimer Decision dated Nov. 26, 2012; Amendment and Response to Non-Final Rejection with Terminal Disclaimer filed Nov. 16, 2012; and Non-Final Rejection dated Aug. 16, 2012.

Office Actions and Responses to Office Actions of related U.S. Appl. No. 13/916,947, filed Jun. 13, 2013: Letter Restarting Period for Response to Final Rejection and Applicant Initiated Interview Summary dated Oct. 21, 2014; Final Rejection dated Aug. 14, 2014; Amendment and Response to Non-Final Rejection dated Jul. 9, 2014; and Non-Final Rejection dated Apr. 9, 2014.

* cited by examiner

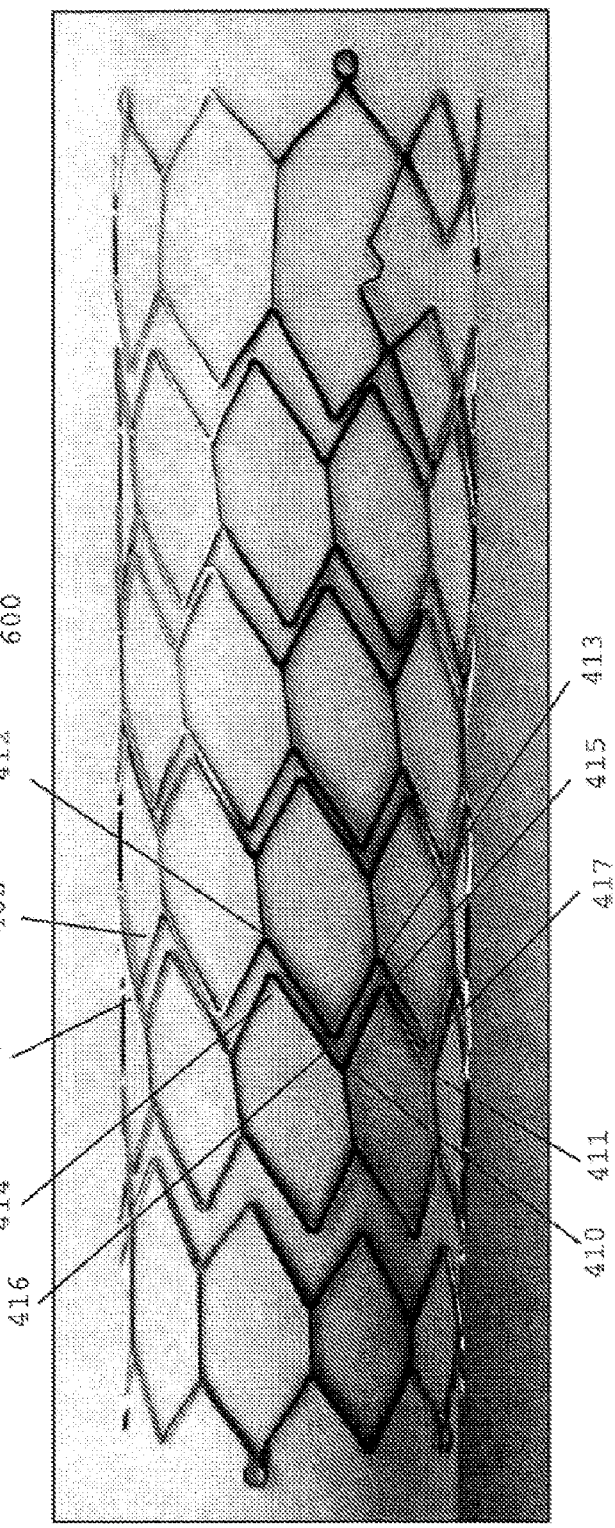

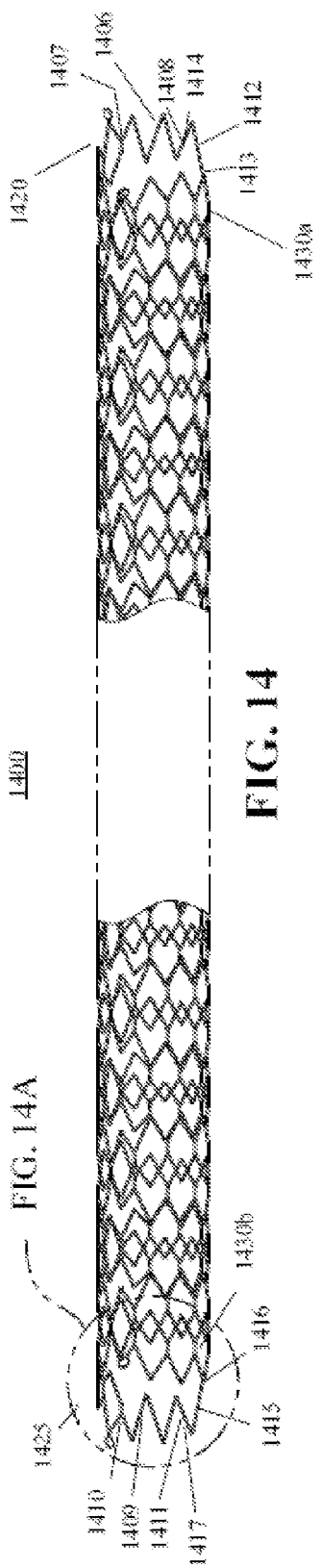

HELICAL HYBRID STENT

CROSS-REFERENCE TO RELATED APPLICATIONS

This application is a continuation-in-part of U.S. application Ser. No. 13/467,800 filed on May 9, 2012, which is a continuation of application Ser. No. 12/428,347 filed on Apr. 22, 2009, issued as U.S. Pat. No. 8,382,821 on Feb. 26, 2013, which is a continuation-in-part of application Ser. No. 11/377,769 filed on Mar. 15, 2006 which is a continuation-in-part of application Ser. No. 11/331,639, filed on Jan. 13, 2006, which is a continuation-in-part of application Ser. No. 10/860,735, filed on Jun. 3, 2004, now abandoned. Application Ser. No. 11/377,769 is also a continuation-in-part of application Ser. No. 10/607,604, filed on Jun. 27, 2003, now abandoned. This application is also a continuation-in-part of U.S. application Ser. No. 12/764,418 filed on Apr. 21, 2010. The entirety of these priority applications is hereby incorporated in toto by reference.

FIELD OF THE INVENTION

The invention relates generally to stents, which are intraluminal endoprosthesis devices implanted into vessels within the body, such as blood vessels, to support and hold open the vessels, or to secure and support other endoprostheses in vessels.

BACKGROUND OF THE INVENTION

Various stents are known in the art. Typically, stents are generally tubular in shape, and are expandable from a relatively small, unexpanded diameter to a larger, expanded diameter. For implantation, the stent is typically mounted on the end of a catheter with the stent being held on the catheter in its relatively small, unexpanded diameter. Using a catheter, the unexpanded stent is directed through the lumen to the intended implantation site. Once the stent is at the intended implantation site, it is expanded, typically either by an internal force, for example by inflating a balloon on the inside of the stent, or by allowing the stent to self-expand, for example by removing a sleeve from around a self-expanding stent, allowing the stent to expand outwardly. In either case, the expanded stent resists the tendency of the vessel to narrow, thereby maintaining the vessel's patency.

Stents may be constructed from tubes or from a flat sheet of metal, which is rolled and fixed such as by welding, mechanical lock or otherwise, to form the tubular structure of the stent.

Some examples of patents relating to stent designs include U.S. Pat. No. 4,733,665 to Palmaz; U.S. Pat. Nos. 4,800,882 and 5,282,824 to Gianturco; U.S. Pat. Nos. 4,856,516 and 5,116,365 to Hillstead; U.S. Pat. Nos. 4,886,062 and 4,969,458 to Wiktor; U.S. Pat. No. 5,019,090 to Pinchuk; U.S. Pat. No. 5,102,417 to Palmaz and Schatz; U.S. Pat. No. 5,104,404 to Wolff; U.S. Pat. No. 5,161,547 to Tower; U.S. Pat. No. 5,383,892 to Cardon et al.; U.S. Pat. No. 5,449,373 to Pinchasik et al.; and U.S. Pat. No. 5,733,303 to Israel et al.

One type of stent is known as the helical or coiled stent. Such a stent design is described in, for example, U.S. Pat. Nos. 6,503,270 and 6,355,059, which are incorporated herein, in toto, by reference. This stent design is configured as a helical stent in which the coil is formed from a wound strip of cells wherein the cells form a serpentine pattern comprising a series of bends. Other similar helically coiled stent structures are known in the art.

One object of prior stent designs has been to insure that the stent has sufficient radial strength when it is expanded so that it can sufficiently support the lumen. Stents with high radial strength, however, tend also to have a higher longitudinal rigidity than the vessel in which it is implanted. When the stent has a higher longitudinal rigidity than the vessel in which it is implanted, increased trauma to the vessel may occur at the ends of the stent, due to stress concentrations on account of the mismatch in compliance between the stented and un-stented sections of the vessel, or otherwise, the rigid stent may interfere with the vessel's natural tendency to bend and to stretch. Conversely, stents with good flexibility often lack sufficient and/or uniform radial support for the vessel wall. Thus, a continued need exists in the art for a stent having a balance of good radial strength and a high degree of longitudinal flexibility.

Another problem in the art arises when trying to simplify the manufacturing process of a stent to reduce costs yet prevent manufacturing defects, while still producing a stent with uniformly high flexibility and sufficient radial support.

SUMMARY OF THE INVENTION

The present invention provides a helical stent that is longitudinally flexible such that it can easily be tracked down tortuous lumens and does not significantly change the compliance of the vessel after deployment, wherein the stent is relatively stable so that it avoids bending or tilting in a manner that would potentially obstruct the lumen and avoids leaving significant portions of the vessel wall unsupported. The stent of the present invention comprises a helical structure maintained by a polymer fiber layer or other securement. Further, this stent has the radial support of a metal stent combined with longitudinal flexibility, conformability and fatigue resistance to longitudinal repeated bending, compression and twisting, that is much higher than that achievable by metal stents.

One embodiment of the invention comprises a main stent component combined with a polymer fiber layer such as, for example, a biocompatible material, wherein the polymer fiber layer maintains the tubular shape of the stent while the main component provides structural support both to the vessel and the polymer fiber layer to prevent sagging of the polymer layer into the lumen upon deployment.

The main stent component may be formed of a ribbon or strip as a continuous elongated component, preferably having spaced undulating portions forming periodic loop portions. The undulating portions are understood to include portions having a generally sinusoidal or zig-zag pattern. The ribbon may be helically wound to produce a helical, tubular structure which can function to hold open a blood vessel upon expansion. The ribbon is designed so as to naturally form a helical, tubular structure upon helical winding such that the individual cycles of the helical coils—defined by the length of the ribbon required to traverse the entire circumference of the resulting tubular structure in the helical direction—are spaced apart from one another across the longitudinal axis of the tubular structure. The stent can also comprise two or more simultaneously wound ribbons, such that the windings of the different ribbons will interchange or alternate along the stent or will be partially or completely overlapped.

Alternatively, the main stent component or helically oriented ribbon may be formed from a tube wherein the tubular structure has been etched or laser cut into the helically coiled structure of the instant invention.

The main stent component forms a tubular structure of helical coils. The distance along the longitudinal axis of the stent between cycles of the helical coils may vary in length depending on the needs of the particular stent.

In another embodiment, the main stent component may be designed such that each undulating coil directly abuts an adjacent undulating coil of the helical structure so that the space between cycles is minimized; that is, the undulating pattern is nestled into an adjacent, substantially similar undulating pattern at different cycles of the helical coils. In this manner, the helical coils of the stent provide enhanced coverage of the wall of the lumen without loss of overall stent flexibility. Because the helical coils may be nestled into one another without directly touching each other, the overall flexibility of the formed stent is unaffected by the proximity of different cycles of the helical coils. This arrangement also prevents potential sagging of the polymer layer connecting the helix. The nestling of elements in adjacent coils can be either by nestling of undulating structures as described above or by nestling of any type of connected elements, connected to the undulating structure. These elements can be straight—stick like—elements aligned with the longitudinal direction of the stent or slanted or curved relative to it.

The main stent component may comprise side bands and end bands. The side bands extend in a parallel fashion along the length of the main stent component. Each preferably comprises an undulating pattern which may intersect directly with one or more adjacent side bands or through cross-struts. End bands may extend from either end of the strip and may be positioned at an angle to the side bands which form the central portion of the ribbon. These end bands may be designed to form a circumferential band or ring around the circumference of the tubular structure at either or both ends of the stent upon formation. The end bands may be tapered and/or affixed with additional elements, such as hooks, polymers, welds or the like to secure the ends of the helical tubular structure. Alternatively, the end bands may be formed by extending the length of a side band such that a single undulating pattern extends in either longitudinal direction of the main stent component. The main stent component may further comprise of one or more hooks extending from either or both side bands at an angle oriented to align with an end band upon formation of a tubular stent. Upon formation of the stent—such as, by example, helically winding the main stent component, the hook may be connected to the end band—either by welding or other means—to form a closed band or ring around the circumference of the stent; the band or ring may be oriented approximately at a right cylinder to the longitudinal axis of the stent.

The main stent component may be formed from amorphous metal alloys, regular metals, or other biocompatible materials. Amorphous metal stents of the invention may be formed of one or more flat sheets of helically wound metal. Because amorphous metal alloys cannot be easily welded without the metal reverting to an undesirable crystalline form, the present invention contemplates wrapping or embedding the helically coiled amorphous metal alloy main stent component in a polymer fiber layer, such as a biocompatible non-metallic material, thereby forming a hybrid stent, where hybrid is taken to mean that the mechanical properties of the stent are a hybrid of a strong radial structure typical for metal and soft, flexible and durable longitudinal structure typical of non-metallic materials.

In one embodiment, the main stent component may be held in its helical coiled form by a polymer layer without requiring welding or otherwise interlocking the helically wound strip to itself. A second stent component, i.e., a securement, may be used to provide longitudinal rigidity and structural support for the tubular shape of the main stent component while aiding in longitudinal flexibility of the stent. The securement is oriented and affixed to the main stent component such that, upon expansion or bending of the stent, the securement contributes to the overall flexibility of the stent while still aiding in maintaining the main stent component in a tubular shape. The securement may comprise fibers, wires, threads, ribbons, strips, polymers, meshes or the like. In another embodiment, the main stent component is held in its helical form by welding or interlocking elements of the helical coils to hold the structure in proper cylindrical shape. Similarly, embodiments are contemplated that would combine polymer and other securement means to maintain the helical structure.

BRIEF DESCRIPTION OF THE DRAWINGS

FIG. 7 illustrates yet another embodiment of the invention wherein the helical main stent component has its coils nestled into one another.

FIG. 14 illustrates a tubular view of the helical main stent component of FIG. 13.

DETAILED DESCRIPTION OF THE INVENTION

Figure 1:
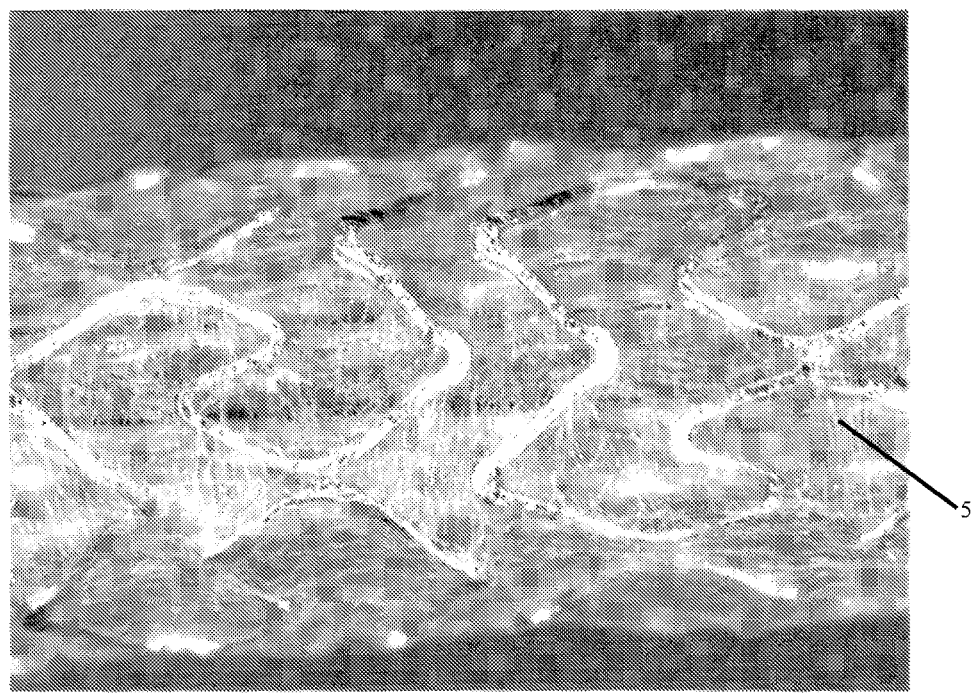
FIG. 1 illustrates a photomicrograph of stent members connected by a porous polymeric fiber structure.

This invention provides a new class of intraluminal prosthetic devices defined as helical hybrid stents. In particular, the stents of the present invention comprise a main stent component in the form of a helical tubular structure. The main stent component may be held in its coiled position by a second component, securing the helical coils into a tubular structure. The second component may be one or more of a variety of means for securing the main stent component in the tubular form. The second component may be, for example, weld points, interlocking means and/or a polymer. In one embodiment, the second component comprises a polymer or polymer fibers which wraps around or embeds itself in the coiled main stent component. The elastic range of the polymer fiber layer must be sufficient to allow expansion of the stent and maximal bending during and after implantation without reaching the elastic limit.

The stent of the present invention may be balloon expandable or self-expanding. When a balloon-expandable stent system is used to deliver the stent, the stent is mounted on the balloon and the catheter assembly is positioned at the implantation site. The balloon is then inflated, radially applying a force inside the stent and the stent is expanded to its expanded diameter. Alternatively, the stent may be self-expanding in which case a balloon is not needed to facilitate expansion and delivery of the stent.

By forming a stent with a single main stent component instead of separate components, the present invention provides for ease of manufacturing a whole stent structure without the necessity of forming multiple components and thereafter joining them to form a stent. The present invention also allows for the manufacturing of a stent formed of two or more simultaneously coiled main stent components which may or may not be of the same material or design, such that the windings of different ribbons may interchange, or alternate over the length of the stent. The present invention also allows for forming a stent from hard-to-weld materials, such as amorphous metal without the need to fix the individual rings.

The present invention relates to a stent comprising a continuous main stent component having side bands containing a periodic series of undulations that is helically arranged, for example, as a coil into a helical, tubular shape. The main stent component may be formed from one or more flat metal ribbons. Alternately, the main stent component may be formed as a tube wherein a helically coiled pattern has been etched or laser cut into it. In either case, the helical stent will have a pattern resembling a coiled ribbon or ribbons, wherein each ribbon comprises two or more parallel side bands each having an undulating pattern.

The side bands are joined together directly and/or through cross-struts. The main stent component may further comprise end bands, which have undulating bands that may extend at an angle from each end of the main stent component at an angle in the general direction of the side bands. The end bands in this orientation each follow the circumferential axis of the helically coiled tubular structure. Alternatively, the end bands may extend in a direction generally parallel with the side bands of the main stent component, oriented to align, upon helical formation of the stent, with hooks extending at an angle from the main stent component. Optionally, the side bands of the ribbon may be tapered without resort to additional end bands. Both the end bands and tapering of the ends of the main stent component allow the ends of the finished stent to be substantially straight; i.e., it allows the stent to form a right cylinder, with each of the ends of the cylindrical stent lying in a plane perpendicular to the longitudinal axis of the stent.

The cross-struts may be straight connectors or may have one or more loops between connection points to side bands and/or end bands. Further, individual cross-struts may connect an end band to an adjacent side band while other cross struts connect two adjacent end bands one to another or two adjacent side bands one to another.

The undulating patterns of the side bands and end bands are such that, in the helically coiled form of the ribbon, the adjacent side bands and/or end bands may be substantially parallel to one another. The undulating patterns are understood to have peaks and troughs. The troughs may be defined by points of connection to the cross-struts or to troughs of the adjacent-most side band or end band. The end bands are arranged at an angle such that the end bands extend about a circumferential axis of the helically coiled main stent component.

The end sections may be formed from the same ribbon which constitutes the side bands. The end sections support the helical coiled structure. Alternatively, the helical coils of the main stent component may be connected by separate end band elements aligned with the longitudinal direction of the stent or slanted relative to it.

The ribbon may be arranged to provide a cellular stent design. The helical main stent component can be any structure which provides a stored length to allow radial expansion. Example designs are described in, but not limited to, U.S. Pat. No. 6,723,119, which is incorporated herein in toto, by reference. Another example design is a stent pattern described in U.S. Pat. No. 7,141,062 ("'062"). The '062 stent comprises triangular cells, by which is meant a cell formed of three sections, each having a loop portion, and three associated points of their joining forming each cell. One or more rows of such cells may be assembled in a ribbon which may be helically coiled from two or more side bands to form a main stent component. Similarly, the cells in the stent described in U.S. Pat. No. 5,733,303 to Israel et al. ("'303") may be used for the main stent component but helically coiled. The '303 patent describes a stent having cells formed of four sections, each having a loop portion and four associated points of their joining forming each cell, also known as square cells. Such square cells may be formed with the side bands and cross struts of the helically coiled ribbon of the present invention. Each of these designs is expressly incorporated herein in toto by reference. Other similarly adaptable cellular stent designs known in the art are readily applicable to the helical stent of the present invention.

Employment of a light and porous or fiber polymeric material in the stents of the present invention provides several advantages. For example, a fibrous material may provide a longitudinal structure thereby enhancing the overall flexibility of the stent device. Such a material may be applied to a tubular stent in a continuous or non-continuous manner depending upon the particular needs of the structure contemplated. Polymeric material can form a porous fiber mesh that is a durable polymer. The longitudinal polymeric structure serves at least two functions. First, the longitudinal polymeric structure is more longitudinally flexible than a conventional metallic structure. Second, the polymeric material is a continuous structure with small inter-fiber distance and can be used as a matrix for eluting drug that would provide a more uniform elution bed. Another advantage of using these materials is that the continuous covering provided by the material after the stent is deployed in a vessel is believed to inhibit or decrease the risk of embolization. Yet another advantage is the prevention of "stent jail" phenomenon, or the complication of tracking into side branches covered by the stent. Further advantage is the high fatigue resistance of polymer structures with high elastic range.

The polymer layer can be disposed within interstices and/or embedded throughout the stent. The polymer layer may secure portions of the stent structure or may fully envelop the entire stent. The polymer layer is a biocompatible material. Biocompatible material may be a durable polymer, such as polyesters, polyanhydrides, polyethylenes, polyorthoesters, polyphosphazenes, polyurethane, polycarbonate urethane, silicones, polyolefins, polyamides, polycaprolactams, polyimides, polyvinyl alcohols, acrylic polymers and copolymers, polyethers, celluiosics and any of their combinations in blends or as copolymers. Of particular use may be silicone backbone-modified polycarbonate urethane and/or expanded polytetrafluoroethylene (ePTFE).

FIG. 1 shows a photomicrograph of an exemplary stent illustrating stent members connected by a porous polymer layer. The stent of FIG. 1 is connected by a polymer layer 5 represented here as a porous longitudinal structure along a longitudinal axis of the stent. Illustrated here, the polymer layer 5 is a porous durable fiber mesh. The polymer layer 5 provides a continuous structure having small inter-fiber distances and forming a matrix. This matrix may be used for eluting a drug and may provide a uniform elution bed over conventional methods. In addition, the polymer layer 5 may function to hold the main stent component in a tubular shape and to prevent unwinding upon expansion and flexing. In addition, the polymer layer 5 enables longitudinal flexibility to the stent structure.FIG. 1 shows a photomicrograph of an exemplary stent illustrating stent members connected by a porous polymer layer. The stent of FIG. 1 is connected by a polymer layer represented here as a porous longitudinal structure along a longitudinal axis of the stent. Illustrated here, the polymer layer is a porous durable fiber mesh. The polymer layer provides a continuous structure having small inter-fiber distances and forming a matrix. This matrix may be used for eluting a drug and may provide a uniform elution bed over conventional methods. In addition, the polymer layer 5 may function to hold the main stent component in a tubular shape and to prevent unwinding upon expansion and flexing. In addition, the polymer layer 5 enables longitudinal flexibility to the stent structure.

The longitudinal structure of the biocompatible polymer layer may be porous or it may be formed as a tube with fenestrations or a series of fibers with spaces between them, to promote growth of neo-intima that will cover the stent and secure it in position. Fenestrations may also promote better stabilization of the stent. The shape of fenestration can be made in any desired size, shape or quantity.

Figure 2:
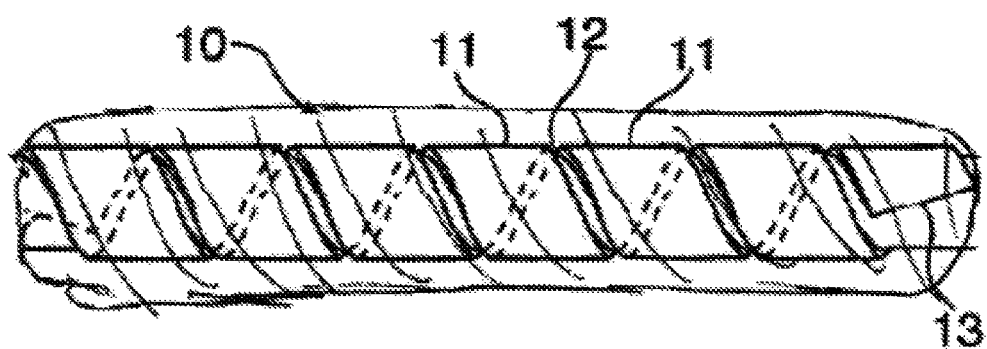
FIG. 2 illustrates stent having a schematic helical component connected by a fiber polymeric structure.

FIG. 2 shows an example helically coiled ribbon 12 disposed in a polymer layer such as a porous fiber mesh 10. As shown in FIG. 2, the stent is formed as a helically wound ribbon having ends 13 and coils 11. Depending on the embodiment, the coils 11 of the ribbon 12 are relatively resistant to longitudinal displacement or tilting because of the width of the ribbon 12. The mesh 10, although allowing longitudinal flexibility of the stent, further provides support to the stent to resist longitudinal displacement or tilting. The ribbon 12 is designed to have a helical tubular shape.

Figure 3:
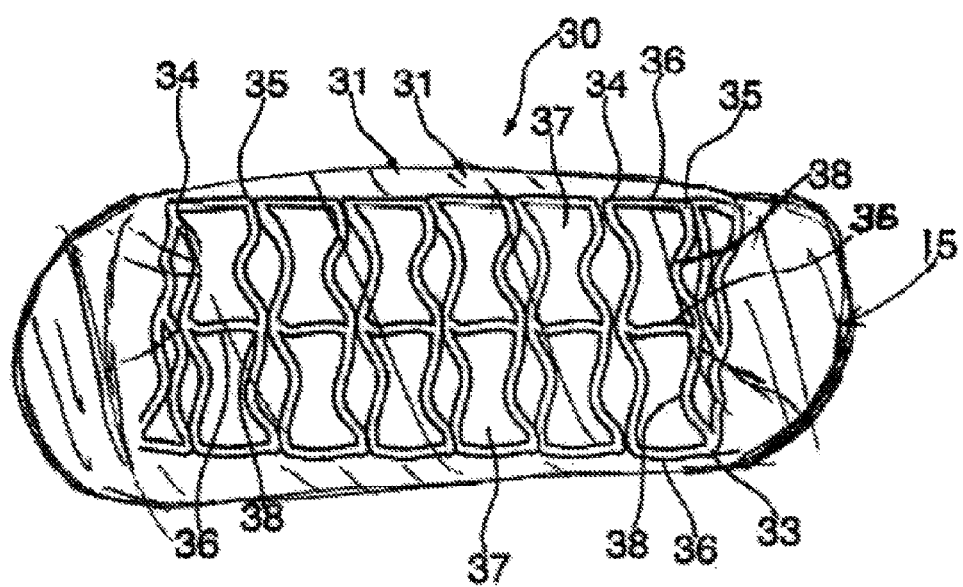
FIG. 3 illustrates one embodiment of a main stent component connected by a fiber polymeric structure.

FIG. 3 shows a serpentine coiled ladder stent 30 constructed in accordance with the invention. The serpentine coiled ladder stent 30 in FIG. 3 is shown having a porous fiber mesh 15 disposed about the stent.

The serpentine coiled ladder stent 30 embodiment illustrated in FIG. 3 is configured as a helical stent in which the coils are formed from a helical strip of cells 37, wherein the sides of the cells 37 are serpentine or contain undulations. The stent in this illustration is comprised of a strip helically wound into a series of helical coils 31, wherein the main stent component is formed of two side bands 34, 35 connected to each other, for example by a series of cross struts 36. Each side band 34, 35 is formed in a serpentine pattern comprising a series of undulations 38. Upon expansion of the stent, the undulations 38 of the side bands 34, 35 open to increase the length of each of the individual cells 37 in the helical direction. Thus, lengthening the strip in the helical direction permits the stent 30 to expand without any significant unwinding of the strip, or foreshortening. In the unexpanded state, the side bands collapse to form a serpentine continuum.

In the illustrated embodiment of FIG. 3, the cross struts 36 joining the side bands 34, 35 to each other are straight and extend in a direction generally perpendicular to the helical direction in which the strip is wound. Alternatively, the cross struts may have one or more bends, and/or they may extend between the two side bands at other angles. In the illustrated embodiment, the cross struts 36 join oppositely facing undulations 38 on the side bands 34, 35, and they are attached to the side bands 34, 35 at every second undulation 38. Alternatively, the cross struts 36 may be joined in other places, and may occur with more or less frequency, without departing from the general concept of the invention. The side bands 34, 35 and the cross struts 36 form the perimeter of each cell. The stent alternatively may be formed without cross struts 36, by having, for example, the two serpentine side bands 34, 35 periodically joined directly to each other at adjacent points.

Furthermore, as shown in FIG. 3, the ends 33 of the serpentine main stent component may be tapered. The tapering of the ends 33 of the main stent component allows the ends of finished stent to be straight, i.e., it allows the stent to take the form of a right cylinder, with each of the ends of the cylindrical stent lying in a plane perpendicular to the longitudinal axis of the stent. The ends 33 of the main stent component may be joined to respective adjacent windings 31 using the porous fiber mesh 15 to join ends 33, for example when made from an amorphous metal.

Figure 4:
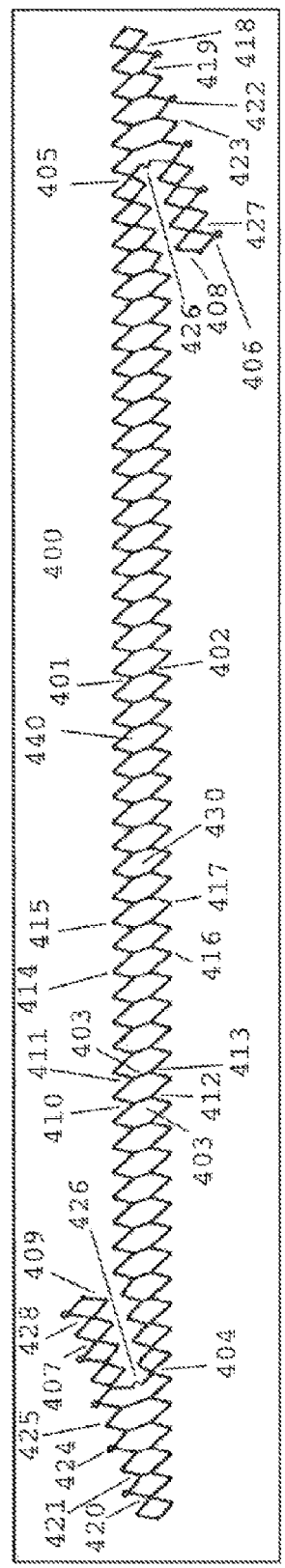
FIG. 4 illustrates a flat ribbon main stent component formed according to one embodiment of the invention.

FIG. 4 illustrates an embodiment of the invention wherein the main stent component is shown in the flatten ribbon form. The main stent component 400 is shown in an uncoiled state, i.e., flat. As depicted in FIG. 4, the main stent component 400 has an undulating design in the longitudinal direction. The undulating design comprises a first side band 401 having an undulating shape and a second side band 402 having an undulating shape. The first side band 401 and second side band 402 are arranged along a generally parallel orientation except at either end of the side bands where the first side band tapers toward the second side band and the second side band tapers toward the first side band. Accordingly, when the main stent component 400 is laid flat as depicted in FIG. 4, the undulations of the first side band 401 comprise troughs (e.g., 410, 411) that face toward the second side band 402 and peaks (e.g., 414, 415) that face away from the second side band 402. Similarly, the undulations of the second side band 402 comprise troughs (e.g., 412, 413) that face toward the first side band 401 and peaks (e.g., 416, 417) that face away from the first side band 401. The first side band 401 and second side band 402 are connected to each other by a plurality of first cross struts 403 to form cells 440. In particular, for example, at least one trough (e.g., 410) of the first side band 401 is connected to a corresponding trough (e.g., 412) of the second side band 402 via a first cross strut 403. Thus, a series of cells are formed, each cell defined individually by the joining of the adjacent side bands to form an enclosed space by cross-struts. For example, in FIG. 4, a cell is defined by the portion of the first side band between troughs 410 and 411, the portion of the second side band between troughs 412 and 413 and the first cross-struts 403 respectively connecting troughs 410 and 412 and inner peaks 411 and 413.

In FIG. 4, the first cross struts 403 connect first side band 401 and second side band 402 at regular intervals, in particular at adjacent troughs, thereby forming cells, e.g., 430. In alternative embodiments, the number of first cross struts 403 may differ from that illustrated in FIG. 4. For example, the first cross-struts 403 may connect the first band 401 and second band 402 at regular intervals at, for example, every second trough, or every third trough, or every fourth trough, etc., thereby making larger cells. In still other embodiments, the first cross struts 403 may connect the first side band 401 and second side band 402 at varying intervals, for example, the varying interval pattern may be: adjacent trough, third trough, adjacent trough, fourth trough, adjacent trough, third trough, etc. (not shown), or another pattern, as may be appropriate for a particular use, thereby making a variety of differently sized cells along the main stent component. The first cross-struts 403 may each have the same width relative to each other and to the side bands 401, 402, as shown in FIG. 4. Alternatively, the first cross-struts 403 may have a different width from the first and second side bands 401, 402, or a different width from each other, as appropriate for a particular use. In addition, first cross-struts 403 may comprise a straight member or may contain one or more loops, thereby forming square cells similar to those taught by the '303 patent or triangular cells as taught in the '062 patent. The cross struts may connect adjacent or offset troughs of the first and second side bands 401, 402. As shown in FIG. 4, differently shaped cross-struts, or no cross-struts may alternatively be employed in a single stent design depending on the particular use of the stent so that a stent having different cell shapes may be formed.

The main stent component 400 in the embodiment depicted in FIG. 4 tapers at each end. In particular, the length of the cross struts 403 shorten toward each end of the main stent component 400, so that the first and second bands 401, 402 become closer together and eventually are connected directly at points of connection 404 and 405. Alternatively, in embodiments without cross struts, the undulations may become more shallow to create a tapered end on the flattened ribbon of the main stent component.

Extending from the end of either side band 401 and 402 in FIG. 4 are end bands 406 and 407. Thus, a first end band 406 extends from the end of the first side band 401 in a direction offset from the general direction of the first side band 401. A second end band 407 extends from the end of the second side band 402 in a general direction offset from the general direction of the second side band 402 and opposite the first end band. The first end band 406 and second end band 407 each have an undulating pattern. The first end band 406 has troughs (e.g. 418, 419) that face toward the first side band 401 and peaks (e.g. 422, 423) that face away from the first side band 401. Likewise, the second end band 407 has troughs (e.g. 420, 421) that face toward the second side band and peaks (e.g. 424, 425) that face away from the second side band 402. The first end band 406 connects directly to the first side band 401 at, e.g., trough 418; however, as the first end band 406 angularly extends away from the first side band, second cross-struts 426 connect the first end band 406 to the first side band 401. Likewise, the second end band 407 connects directly to the second side band 402 at, e.g., trough 420; however, as the second end band 407 angularly extends away from the second side band, second cross-struts 426 connect the second end band 407 to the second side band 402. As depicted in FIG. 4, the second cross struts 426 may contain one or more loops between points of connection with adjacent end bands and/or side bands. The peaks of the first end band 406 and second end band 407 optionally may have additional circular structures extending from the peaks (e.g. 423, 424) as depicted by FIG. 4.

In addition, a third end band 408 is arranged generally parallel to first end band 406, with troughs facing each other and connecting directly, e.g. 427, to said first end band. A fourth end band 409 is arranged generally parallel to second end band 407, with troughs facing each other and connecting directly, e.g. 428, to said second end band. The third end band 408 and fourth end band 409 each have an undulating pattern.

Figure 5:
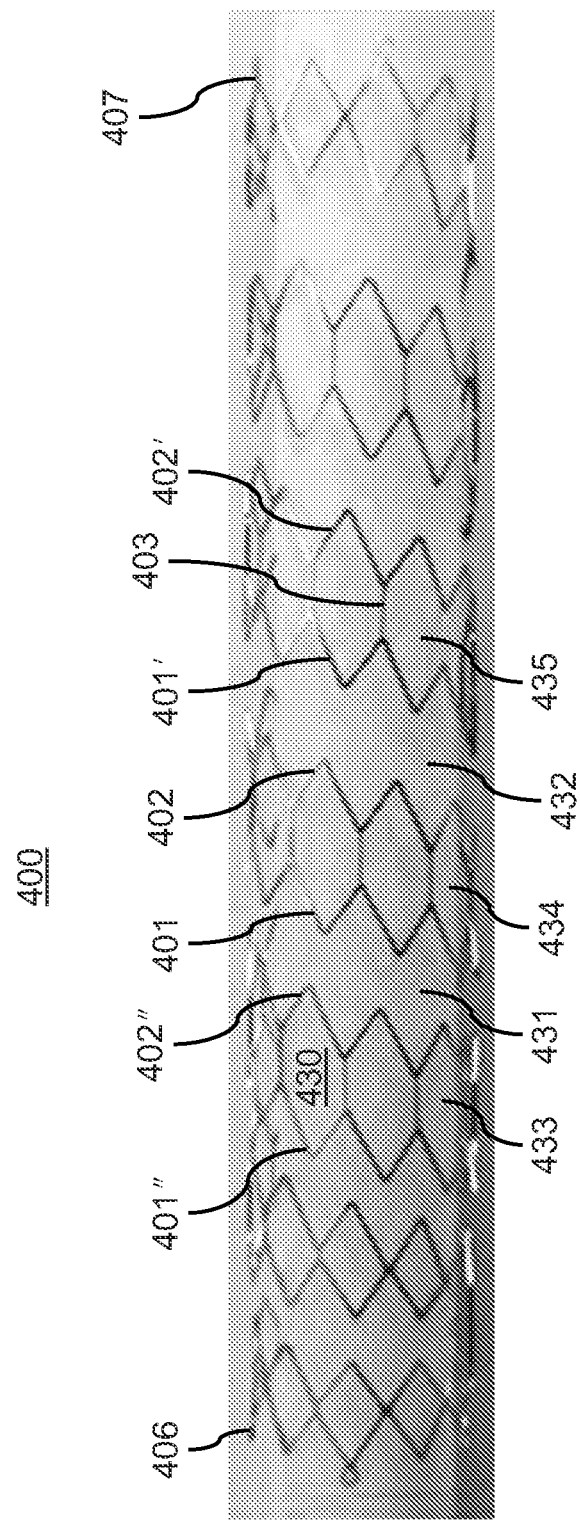
FIG. 5 illustrates a helical main stent component according to the invention having variable distances between helical coils.

FIG. 5 illustrates a helically coiled stent wherein the main stent component 400 forms a tubular structure and the end bands of the ribbon secure the ends of the tubular structure. The undulating design of the main stent component 400 forms a helical, tubular structure, in which the coils of the helix self-arrange to create variable and/or uniform spacing along the longitudinal axis of the tubular structure, e.g. 431, 432, between helical cycles, e.g. 433, 434, 435, as depicted in FIG. 5. Because the stent 400 forms a helix, the first side band 401 and the second side band 402 of the ribbon, may be spaced apart to various extents.

Figure 6:
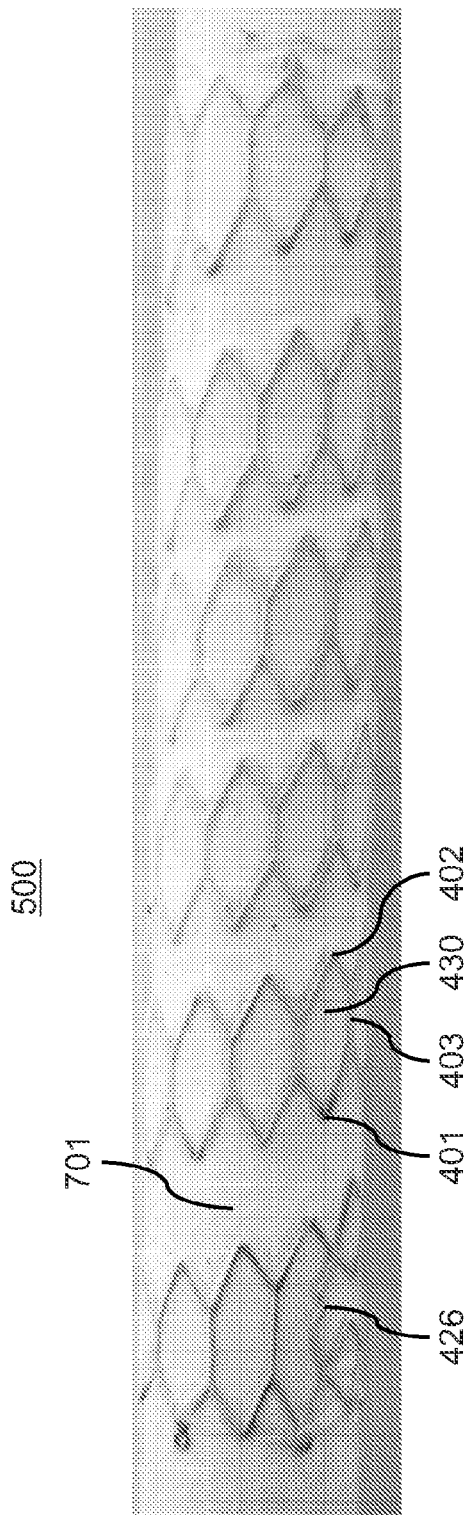
FIG. 6 illustrates another embodiment of the invention having a helical main stent component having side bands and end bands, detailing varying cross struts, and embedded in a polymer.

The helical main stent component 500 may also be secured by embedding the tubular structure in a longitudinal polymer layer as in FIG. 5 and/or FIG. 6, rather than by locking mechanisms or welding alone. The longitudinal polymer layer comprises a biocompatible material. The stent in FIG. 6 is rotated slightly compared to that in FIG. 5 so that the second cross-strut 426 having a loop is visible. Also identified are the first band 401, the second band 402, a first cross strut 403, and a cell 430.

FIG. 7 illustrates a stent according to the invention wherein the helical coils are positioned so that little or no substantial longitudinal space exists between cycles of the helical coils. That is, as illustrated by FIG. 7, the peaks (e.g. 414, 415) of the first side band 401 nestle into the circumferential area created by the peaks (e.g. 416, 417) of the second side band such that the peaks 414, 415 of the first side band 401 approach the troughs 412, 413 of the second side band 402; yet, the first side band 401 remains substantially parallel to the second side band 402. Likewise, the peaks (e.g. 416, 417) of the second side band 402 nestle into the circumferential area created by the peaks (e.g. 414, 415) such that the peaks 416, 417 of the second side band 402 are in close proximity to the troughs 410, 411 of the first side band 401. It may be desirable to position the nestled side bands so that no direct contact occurs between first side band 401 and second side band 402. Because the first side band 401 and the second side band 402 have substantially similar design, the first side band 401 and the second side band 402 can approach one another in this fashion over the entire length of the formed stent. In this manner, the first side band 401 and the second side band 402 may be described as nestled to one another. The stent of FIG. 7 has the additional advantage that the nestled pattern of adjacent first and second side bands minimizes the unsupported areas of the vessel wall and/or polymer layer to prevent sagging of the polymer layer into the lumen upon expansion without any loss of flexibility to the stent. In addition, the nestling of the helical coils separately facilitates the maintenance of the structure in the tubular form.

Figure 8A:
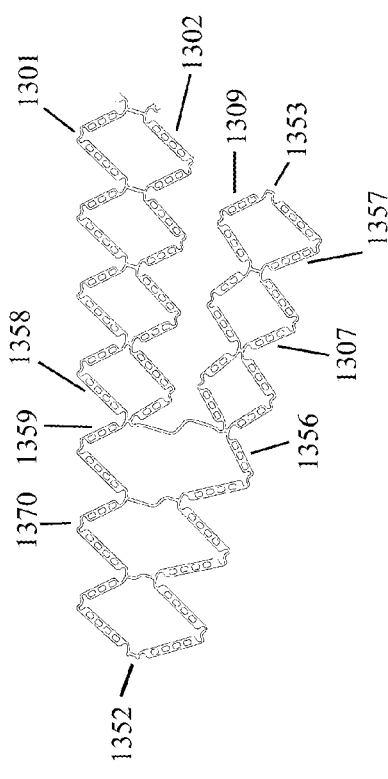
FIG. 8A is an enlarged view of an end band of the main stent component of FIG. 8.
Figure 8:
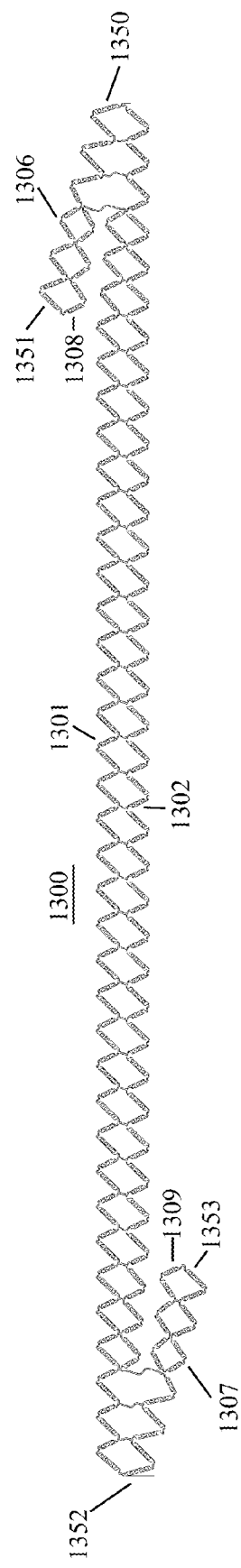
FIG. 8 illustrates an embodiment of a main stent component composed of a flat ribbon having a patterned band and comprises struts with one or more exemplary fenestrations.

FIG. 8 illustrates an alternative embodiment wherein the main stent component 1300 is laid out in flat form, i.e., uncoiled. As depicted, the main stent component 1300 has a patterned band in the longitudinal direction. Like the embodiment of FIG. 4, the design of the main stent component 1300 in FIG. 8 contains a first side band 1301, a second side band 1302, a first end band 1306, a second end band 1307, a third end band 1308 and a fourth end band 1309. In the tubular form, side bands 1301 and 1302 form a continuous helical winding for the central portion of the stent body while first and second end bands 1306 and 1307 form right cylinders to the longitudinal axis of the stent for the end rings of the stent. In the first end band, first edge 1350 is brought together with second edge 1351 while, in the second end band, first edge 1352 is brought together with second edge 1353. Main stent component 1300 comprises struts having one or more fenestrations into which a therapeutic substance may be deposited.

Each band is formed with struts of sufficient width to include one or more fenestrations as shown, for example, in FIG. 8. The fenestrated struts of main stent component 1300 may be of any geometric shape, including, but not limited to, round, oval or rectangular. Further, the fenestrations may extend through the entire thickness of the strut (full fenestrations), or may extend only partially through (partial fenestrations), being open only on one side of the strut (luminal or abluminal in the tubular form). Also, the stent may have struts containing fenestrations having variable sizes, numbers and shapes on one strut or between different struts. The invention contemplates struts having full and/or partial fenestrations on either or both of the side and/or end bands. The struts defining the peaks and troughs of the side bands may vary in length along the length of the main stent component to accommodate the desired shape for the resulting helically coiled stent structure and the number of fenestrations. For example, in FIG. 8A, side band struts 1358 and 1359 differ in length as do end band struts 1356 and 1357. The fenestrated struts are connected by loops or turns 1370 wherein the material is narrower than that of the fenestrated struts to provide enhanced flexibility.

Figure 9:
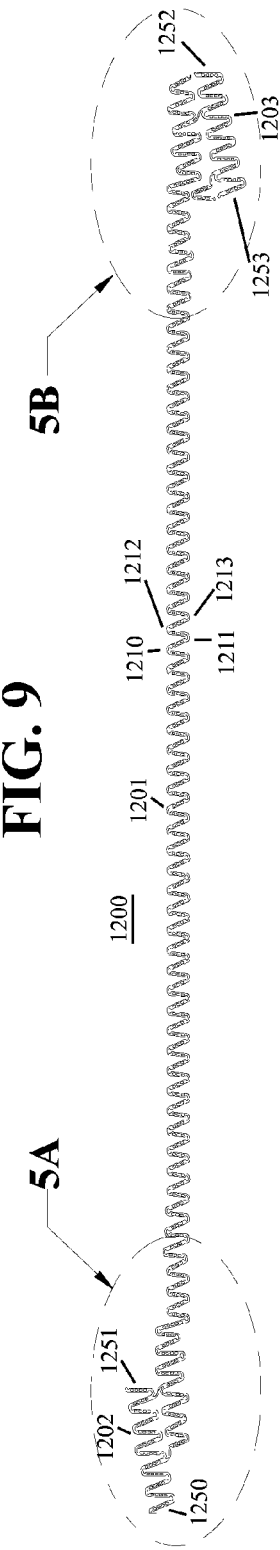
FIG. 9 illustrates a flat ribbon view of a main stent component having undulations and comprising struts with one or more exemplary fenestrations.

FIG. 9 illustrates yet another embodiment of the invention where the main stent component 1200 is laid out in flat form, i.e., uncoiled. As depicted, the main stent component 1200 is a single side band 1201 in the longitudinal direction when laid flat. Side band 1201 is attached to first end band 1202 and second end band 1203 by cross-struts 1240 and 1241, respectively. Side band 1201 comprises an alternating pattern of peaks (e.g., 1210, 1212) and troughs (e.g., 1211, 1213) defined by struts having the same or variable lengths. Each side and end band is formed with struts having sufficient width to include one or more full or partial fenestrations, as described above for FIG. 8, and are also applicable to FIG. 9. The fenestrated struts are connected by loops or turns 1270 that are narrower than that of the fenestrated struts to provide enhanced flexibility. As shown in FIG. 9A, the struts are of varying length and vary in the number of fenestrations in each strut. For example, strut 1217 has a different length and number of fenestrations than strut 1215. Strut 1216 has a different length but the same number of fenestrations than strut 1215. And struts 1214 and 1215 have the same lengths and number of fenestrations. The stent of FIG. 9A contemplates that struts (e.g., 1217) near the ends of the first side band 1201 may have different lengths than struts 1214 and 1215 and are configured to aid in helical winding.

End bands 1202 and 1203 form circumferential end rings in its tubular formd. The first end band 1202 and second end band 1203 extend from the ends of the side band 1201 in a direction angularly offset from the general direction of the side band 1201. End bands 1202 and 1203 are configured to form right cylinders at the ends of the stent, flanking the helical windings of the central stent body upon winding of the structure into a stent. First end band 1202 has first edge 1250 and second edge 1251. In the tubular form, first edge 1250 is brought together with second edge 1251 to form a right cylinder to the longitudinal axis of the stent. Second end band 1203 has first edge 1252 and second edge 1253. In the tubular form, first edge 1252 is brought together with second edge 1253 to form a right cylinder to the longitudinal axis of the stent. As further explained below, the edges (1250 and 1251; 1252 and 1253) may be permanently affixed, or as an alternative, may be held in position with a securement which may keep the two edges in close proximity to maintain a right cylinder to the longitudinal axis of the stent.

In FIG. 9A, first end band 1202 comprises a set of undulations. The direction of the first end band 1202 is offset at an angle to the direction of the side band 1201. In FIG. 9A, the first end band extends from the side band is at an angle less than 45 degrees to the central body of the stent when the stent is laid flat. The undulating pattern of the first end band 1202 comprises alternating peaks (e.g., 1219, 1221) and troughs (e.g., 1220, 1222). Troughs (1220, 1222) of the first end band extend in the direction of the side band while the peaks (1219, 1221) point away from the side band. First end band 1202 also may contain struts having fenestrations. In FIG. 9A, cross-links 1240 and 1242, for example, connect the side band to the first end band. Cross-links 1240 and 1242 extend from the troughs of the first end band to the peak of the side band. Cross-links extending between the side band and the first end band are flexible connectors having one or more curved portions. The invention also contemplates an embodiment where the cross-links may contain one or more loops.

Figure 9B:
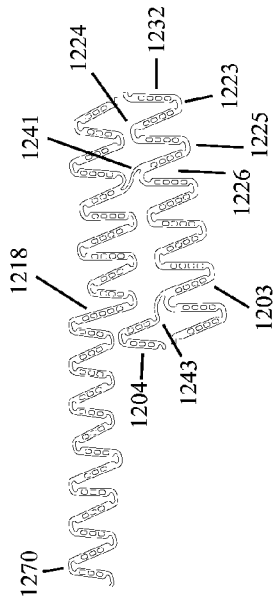
FIG. 9B is an enlarged flat ribbon view of a second end band of FIG. 9.
Figure 9A:
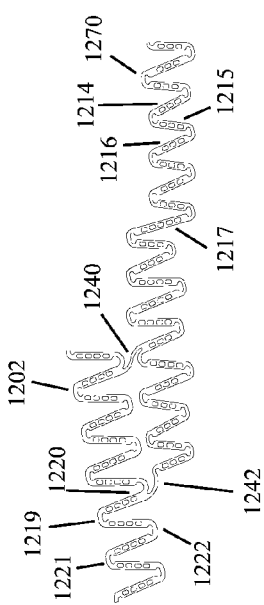
FIG. 9A is an enlarged flat ribbon view of a first end band of FIG. 9.

In FIG. 9B, second end band 1203 also comprises a set of undulations. The direction of the second end band 1203 is angularly offset to the direction of the side band 1201. Preferably, the second end band extends from the side band at an angle less than 45 degrees to the central body of the stent when the stent is laid flat. The undulating pattern of the second end band 1203 comprises alternating peaks (e.g., 1223, 1225) and troughs (e.g., 1224, 1226). Troughs (1224, 1226) of the second end band extend in the direction of the side band while the peaks (1223, 1225) point away from the side band. Second end band 1203 may contain struts having fenestrations. In FIG. 9B, cross-link 1241 connects the side band to the second end band. Cross-link 1241 extends from the trough of the second end band to the trough of the side band. Cross-links extending between the side band and second end band are flexible connectors having one or more curved portions. Cross-links connecting the side band to the second end band may comprise at least one loop.

In addition, the invention contemplates other end bands similar in construction to first and second end bands and connected to either the first or second end bands to facilitate helical winding and uniform coverage. In FIG. 9B, a third end band 1204 having fenestrated struts is connected to the second end band by cross-link 1243. As illustrated in FIGS. 5A 8A and 58B, the invention contemplates first and second end bands which are not identically connected to the undulating or patterned side bands and which are not identical to each other. Like the side band, any one or all the end bands may comprise struts sufficiently wide to accommodate one or more full or partial fenestrations which are connected together with loops having a narrower gauge than the fenestrated struts.

The main stent component may be held in a helically wound position by a second component, securing the helical windings into a tubular structure. The second component, referred to herein as a securement, may be one or more of a variety of means for securing the main stent component in the tubular form. The second component may be, for example, weld points, interlocking means and/or a polymer. The securement maintains the helical winding of the central stent body and/or the formation of right cylinders by the end bands. In one embodiment, the securement comprises a structure in the form of fibers, sheets, threads or ribbons which are wrapped around or itself embedded in the coiled main stent component. In another embodiment, wires or ribbons formed of a metal or non-metal material maintain the main stent component in its tubular configuration. The securement comprises a material that allows flexibility and expansion of the helical main stent component without tearing or detachment of the securement and allows movement between the coiled windings of the main stent body relative to each other. Such a material may be applied to a tubular stent in a continuous or non continuous manner depending upon the particular needs of the structure contemplated.

Preferably, the securement allows expansion of the stent and maximal bending during and after implantation without reaching the elastic limit. The elastic range may be a product either of inherent elasticity in the material used, such as with certain polymers, or of the inclusion of a reserve length of a non-elastic material between points of connection with the main stent component. Yet another advantage of a securement is the prevention of "stent jail" phenomenon, or the complication of tracking into side branches covered by the stent. A further advantage is the high fatigue resistance of particular securement structures with high elastic range.

In one embodiment, the securement is a polymer that is a biocompatible material. Biocompatible material may be durable, such as polyesters, polyanhydrides, polyethylenes, polyorthoesters, polyphosphazenes, polyurethane, polycarbonate urethane, silicones, polyolefins, polyamides, polycaprolactams, polyimides, polyvinyl alcohols, acrylic polymers and copolymers, polyethers, celluiosics and any of their combinations in blends or as copolymers. Of particular use may be silicone backbone-modified polycarbonate urethane and/or expanded polytetrafluoroethylene (ePTFE). Any polymer having a high elastic ratio (high elongation factor within the elastic range) is particularly suitable for a securement. The polymer may also be porous. In embodiments where the polymer a continuous structure with small inter fiber distance, it may also be used as a matrix for eluting drug thereby providing a uniform elution bed. This type of porous securement may be applied to any other stent structure.

Figure 10:
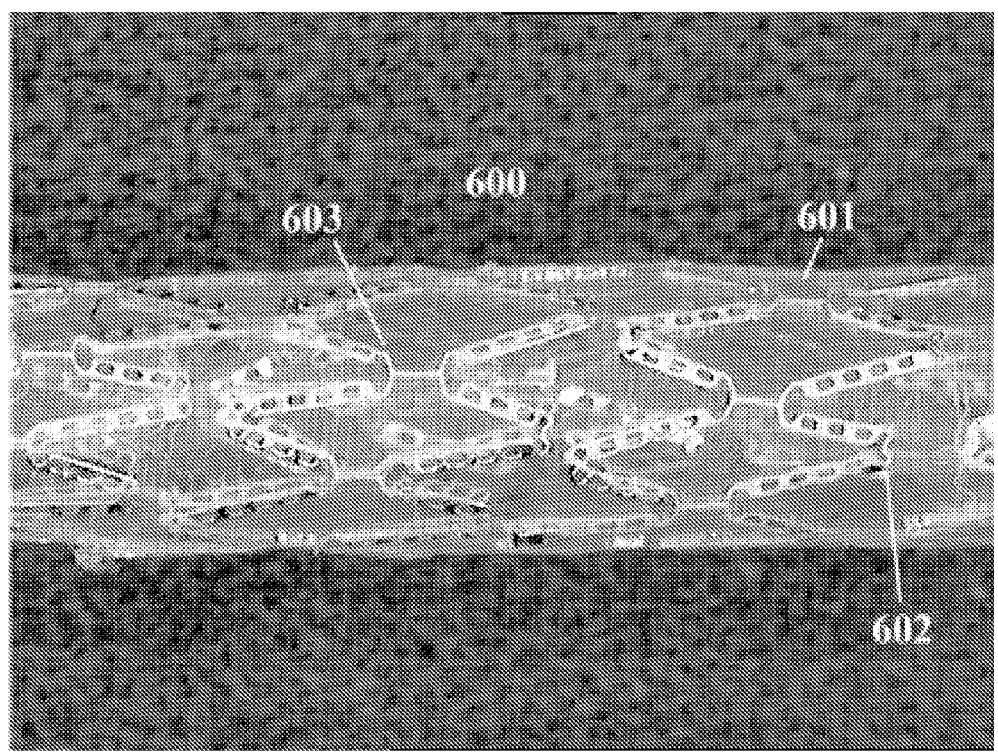
FIG. 10 illustrates a photograph of a securement structure and a main stent component.

FIG. 10 shows the coiled main stent component 600 of FIG. 8, described above, wherein a porous and durable polymer securement 601 is applied over main stent component 600. Two adjacent struts of a first side band are connected to one another by turn 602, which includes a "dimple". The inclusion of a dimple in the turns is an optional feature depending upon the desired properties of the resulting stent. FIG. 10 also illustrates turn 603 which is without a dimple, and is employed in this embodiment at points where crossstruts connect the first side band to the second side band.

Polymeric securements as described above may also be employed in the form of threads, wires or ribbons, thereby securing the main stent component through, for example, a series of points of connection with the main stent component. One or more securement threads, wires or ribbons may be coiled around the stent in a helically different direction than the main stent component. In particular, the thread, wire or ribbon may be coiled around the stent in the reverse helical orientation from the direction of the helically wound strip. Alternatively, securements may be arranged along a longitudinal axis of the stent. Arranged in any non-parallel direction with the main stent component, each thread, wire or ribbon may overlap with the main stent component in a regular pattern across the length of the stent and may effectively function to secure the helical stent body structure. The securement thread, wire or ribbon may be affixed to the main stent component at one or more points of overlap through a variety of means, e.g., welding, bonding, embedding, braiding, weaving, crimping, tying, press fitting or the like, including also joining by adhesive means, e.g., gluing, dip coating, spray coating or the like. The polymeric securement may also be injected into a mold with or without the stent and hence become integrated within the stent. The threads, wires or ribbons maintain the tubular shape of the stent, while the longitudinally flexible quality of the polymeric material discussed above will enhance the overall flexibility of the stent.

Figure 11:
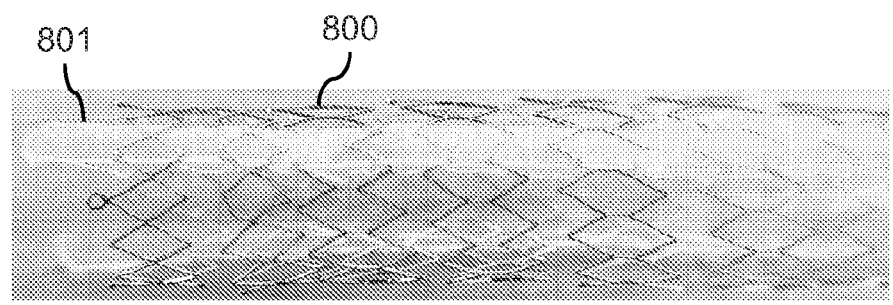
FIG. 11 illustrates an embodiment of the helical main stent component embedded in several ribbon securements.

FIG. 11 illustrates a helically coiled stent wherein the main stent component 800 forms a helically oriented tubular structure that is secured in place by two ribbons 801. The ribbons 801 are a polymeric material that extend along the length of the stent. The ribbons may be affixed to the outside or the inside surface of the stent, or may be embedded in the helically coiled main stent component. In FIG. 11, the main stent component 800 is embedded within each ribbon 801 at points where the main stent component 800 and each second component ribbon 801 intersect.

Figure 12:
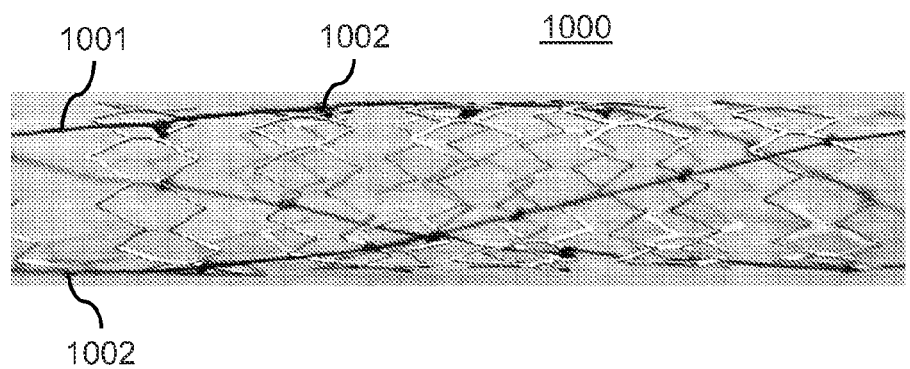
FIG. 12 illustrates a helical main stent component maintained by a plurality of helical securements fastened at discrete points.

FIG. 12 illustrate a helically coiled stent wherein the main stent component 1000 forms a tubular structure similar to FIG. 5 and one or more securement wires 1001 are coiled in a different helical direction to that of the coiled central body portion of the stent. The securement wires 1001 are affixed to the main stent component 1000 at various points of connection 1002 along the stent, thereby maintaining the helical, tubular structure.

In addition to polymeric securements, any other suitable material, including metals and/or non-metals, may be employed as securements in the form of threads, wires or ribbons to secure the main stent component. The metal or non-metal securement wire, thread or ribbon may be affixed to the main stent component where they overlap through one or more of a variety of means as identified above. If the material employed to manufacture the second component is of a lesser longitudinal flexibility than desired, increased flexibility may be achieved by increasing the length of the thread, wire or ribbon between points of connection, thereby providing reserve length of the second component that can extend upon expansion or bending of the stent.

Figure 13:
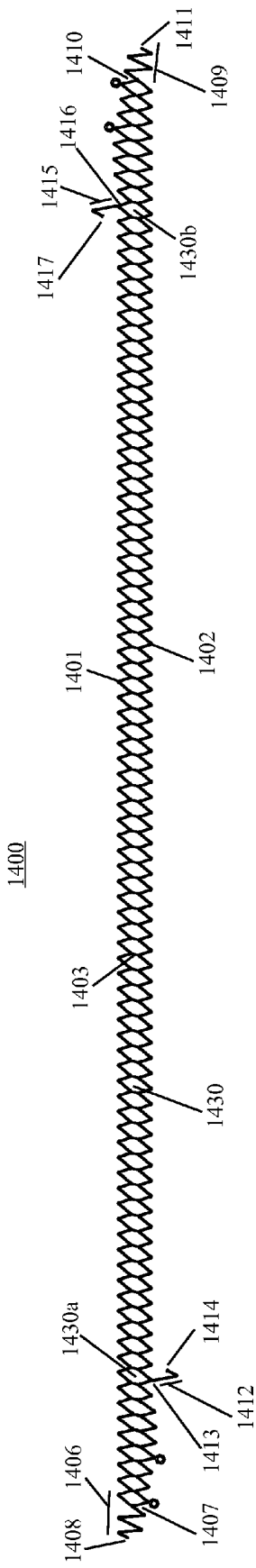
FIG. 13 illustrates a flat ribbon view of a main stent component having side bands with undulations with end bands having undulations extending from either end of the side bands, as well as hooks extending from each of the side bands.

FIG. 13 illustrates an embodiment of the invention wherein the main stent component is shown, for illustration purpose only, in the flatten ribbon form. The main stent component 1400 has a cellular design, comprising a first side band 1401 having an undulating shape and a second side band 1402 having an undulating shape. The first side band 1401 and second side band 1402 are arranged in a generally parallel orientation except at either end of the side bands where, on one end the first side band tapers toward the second side band and on the other end the second side band tapers toward the first side band. The first side band 1401 and second side band 1402 are connected by struts 1403 to form cells 1430. Extending from the end of either side band 1401 and 1402 in FIG. 13 are end bands 1406 and 1409. Thus, a first end band 1406, comprising a series of struts forming a first undulating pattern, extends from the end of the first side band 1401 in a direction generally parallel with the first side band 1401. The first end band 1406 has a first end 1407, located at the point at which the second side band 1402 tapers to connect with the first side band 1401, and a second end 1408 with a plurality of undulations therebetween. A second end band 1409, comprising a series of struts forming a second undulating pattern, extends from the end of the second side band 1402 in a direction generally parallel with the second side band 1402. The second end band 1409 has a first end 1410, located at the point at which the first side band 1401 tapers to connect with the second side band 1402, and a second end 1411 with a plurality of undulations therebetween. The first end band 1406 and second end band 1409 are each formed by an undulating pattern.

Extending from the main stent component is a first hook 1412 and a second hook 1415. The first hook 1412 extends directly from the second side band 1402 and has a first end 1413 that connects directly to a cell 1430a near one end of the main stent component 1400. The first hook 1412 further has a second end 1414. The second hook 1415 extends directly from the first side band 1401 and has a first end 1416 that connects directly to a cell 1430b near the opposite end of the main stent component 1400 from cell 1430a. The second hook further has a second end 1417. The first hook 1412 and the second hook 1415 extend in opposite directions from each other relative to the main stent component 1400. The first hook 1412 is positioned and oriented such that the second end 1414 of the first hook 1412 will align with the second end 1408 of the first end band 1406 in the tubular form of the stent. The second hook 1415 is positioned and oriented such that the second end 1417 of the second hook 1415 will align with the second end 1411 of the second end band 1409 in the tubular form of the stent.

The cells 1430 of the main stent component 1400 may be formed in a variety of sizes and shapes. FIG. 13 illustrates an embodiment of the invention wherein the main stent component 1400 has cells 1430 that are increasingly smaller at either end, corresponding with the tapering of the first side band 1401 towards the second side band 1402 at one end, and the tapering of the second side band 1402 towards the first side band 1401 at the other end.

Figure 14A:
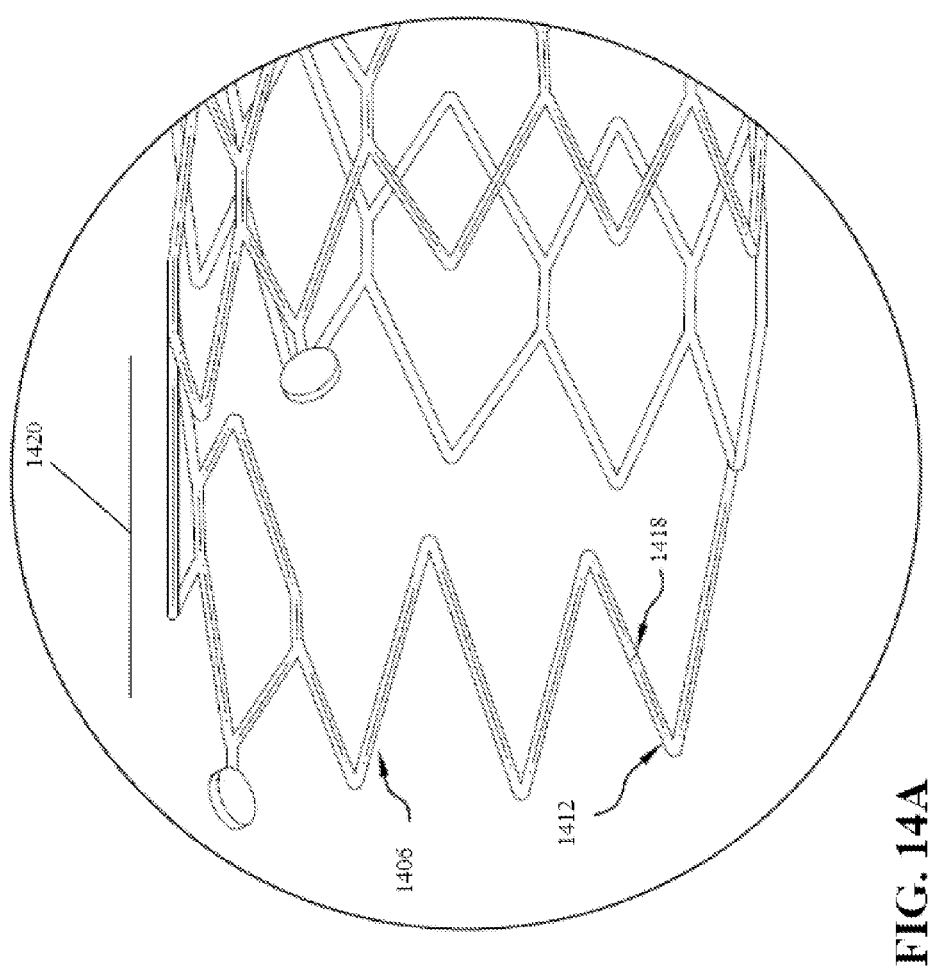
FIG. 14A is an enlarged partial view of the stent of FIG. 14.

FIG. 14 illustrates the main stent component 1400 in the tubular form, e.g. helically wound. As shown in FIG. 14A, which illustrates an enlarged portion of the stent of FIG. 14, the first end band 1406 is connected to the first hook 1412 at connection point 1418, e.g. by welding. Thus, the first end band 1406 and first hook 1412, thereby forming a first cylinder 1420, which is approximately a right cylinder, at one end of the stent. Likewise, the second end band 1409 and second hook 1415 form a second cylinder 1425, which is also approximately a right cylinder, at the other end of the stent.

The end bands may be understood alternatively as continuations of the side bands, such that—for example—first end band 1406 is an extension of the first side band 1401, formed by an undulating pattern extending from the point of connection 1407 where the second side band 1402 tapers to connect with the first side band 1401. Likewise, the second side band 1409 may be understood as an extension of the second side band 1402, formed by an undulating pattern extending from the point of connection 1410 where the first side band 1401 tapers to connect with the second side band 1402.

When the stent of the invention comprises an amorphous metal alloy, it provides the further advantage of enhanced corrosion resistance, resistance to unwanted permanent deformation and higher strength for a given metal thickness. Stents of the present invention comprising amorphous metal alloys exhibit significantly lower conductance or are non-conductive, compared to their crystalline or polycrystalline counterparts. Many medical uses for stents can benefit from such enhanced physical and chemical properties. One embodiment of this invention contemplates intraluminal prosthetic devices comprising at least one amorphous metal alloy combined with components made of other materials, with biocompatible materials being required. This embodiment of the invention may contain one or more amorphous metal alloys. Such alloys provide improved tensile strength, elastic deformation properties, and reduced corrosion potential to the devices.

Amorphous metal alloys, also known as metallic glasses, are disordered metal alloys that do not have long-range crystal structure. Many different amorphous metal alloy compositions are known, including binary, ternary, quaternary, and even quinary alloys. Amorphous metal alloys and their properties have been the subject of numerous reviews (see, for example, *Amorphous Metal Alloys*, edited by F. E. Luborsky, Butterworth & Co, 1983, and references therein). In certain embodiments, the amorphous metal alloys may comprise a metalloid, non-limiting examples of which include silicon, boron, and phosphorus. One possible amorphous metal alloy is an Fe—Cr—B—P alloy. Many other similar alloys are suitable and known to one of ordinary skill in the art.

The stents of the present invention may contain amorphous metal alloys made in a continuous hot extrusion process, as described herein, which possess physical and chemical properties that make them attractive candidates for use in medical devices. For example, amorphous metal alloys may have a tensile strength that is up to ten-fold higher than that of their conventional crystalline or polycrystalline metal counterparts. Also, amorphous metal alloys may have a ten-fold wider elastic range, i.e., range of local strain before permanent deformation occurs. These are important features in medical devices to provide an extended fatigue-resistant lifespan for devices that are subjected to repeated deformations in the body. In addition, these features allow production of smaller or thinner devices that are as strong as their bulkier conventional counterparts.

In other embodiments, the device may contain one or more non-amorphous metals. For example, the device may have components constructed of stainless steel, cobalt chromium ("CoCr"), NiTi or other known materials. With regard to NiTi, the contemplated component may be formed by etching a flat sheet of NiTi into the desired pattern. The flat sheet is formed by rolling the etched sheet into a tubular shape, and optionally welding the edges of the sheet together to form a tubular stent. The details of this method, which has certain advantages, are disclosed in U.S. Pat. Nos. 5,836,964 and 5,997,973, which are hereby expressly incorporated by reference. Other methods known to those of skill in the art such as laser cutting a tube or etching a tube may also be used to construct a stent of the present invention. A NiTi stent, for example, may be heat treated, as known by those skilled in the art, to take advantage of the shape memory characteristics and/or its super-elasticity.

The amorphous metal alloy or other non-amorphous metal components of this invention may also be combined or assembled with other components, either amorphous metal or otherwise, in order to form intraluminal stents. For example, the amorphous metal alloy or other non-amorphous metal components may be combined with a polymer layer such as a biocompatible polymer, a therapeutic agent (e.g., a healing promoter as described herein) or another metal or metal alloy article (having either a crystalline or amorphous microstructure).

The method of combining or joining the amorphous metal alloy or other non-amorphous metal components to other components can be achieved using methods that are well known in the art. Particularly in the case of non-amorphous metals, the helically coiled main stent component may be secured or otherwise intertwined or joined at the ends to the adjacent helical coils. For example, a biocompatible polymer layer covering all or part of the main stent component may be used to secure the helical coils in its tubular shape for positioning and expansion in the lumen. Other non-limiting examples of securement methods including physical joining (e.g., braiding, weaving, crimping, tying, and press-fitting) and joining by adhesive methods (e.g., gluing, dip coating, and spray coating). Combinations of these methods are also contemplated by this invention.

As a further advantage of the invention, the biocompatible structure may be embedded with drug that will inhibit or decrease cell proliferation or will reduce restenosis. Non-limiting examples of such drugs include for example sirolimus, rapamycin, everolimus and paclitaxol, and analogs of these. In addition, the stent may be treated to have active or passive surface components such as drugs that will be advantageous for a longer time after the stent is embedded in the vessel wall.

Various methods of making amorphous metal alloys are known in the art, examples of which are described further below. While preferred embodiments may be shown and described, various modifications and substitutions may be made without departing from the spirit and scope of the present invention. Accordingly, it is to be understood that the present invention is described herein by way of example, and not by limitation.

Methods of Making Amorphous Metal Alloys

Many different methods may be employed to form amorphous metal alloys. A preferred method of producing medical devices according to the present invention uses a process generally known as heat extrusion, with the typical product being a continuous article such as a wire or a strip. The process does not involve additives commonly used in the bulk process that can render the amorphous metal alloy non-biocompatible and even toxic. Thus, the process can produce highly biocompatible materials. In preferred embodiments, the continuous amorphous metal alloy articles are fabricated by a type of heat extrusion known in the art as chill block melt spinning Two common chill block melt spinning techniques that produce amorphous metal alloy articles suitable for the medical devices of the present invention are free jet melt-spinning and planar flow casting. In the free jet process, molten alloy is ejected under gas pressure from a nozzle to form a free melt jet that impinges on a substrate surface. In the planar flow method, the melt ejection crucible is held close to a moving substrate surface, which causes the melt to be simultaneously in contact with the nozzle and the moving substrate. This entrained melt flow dampens perturbations of the melt stream and thereby improves ribbon uniformity. (See e.g., Liebermann, H. et al., "Technology of Amorphous Alloys" Chemtech, June 1987). Appropriate substrate surfaces for these techniques include the insides of drums or wheels, the outside of wheels, between twin rollers, and on belts, as is well known in the art.

Suitable planar flow casting and free-jet melt spinning methods for producing amorphous metal alloy components for the medical devices of this invention are described in U.S. Pat. Nos. 4,142,571; 4,281,706; 4,489,773, and 5,381,856; all of which are hereby incorporated by reference in their entirety. For example, the planar flow casting process may comprise the steps of heating an alloy in a reservoir to a temperature 50-100° C. above its melting temperature to form a molten alloy, forcing the molten alloy through an orifice by pressurizing the reservoir to a pressure of about 0.5-2.0 psig, and impinging the molten alloy onto a chill substrate, wherein the surface of the chill substrate moves past the orifice at a speed of between 300-1600 meters/minute and is located between 0.03 to 1 millimeter from the orifice. In embodiments involving free-jet melt spinning, the process may comprise the steps of heating an alloy in a reservoir to a temperature above the melting point of the alloy, ejecting the molten alloy through an orifice in the reservoir to form a melt stream with a velocity between 1-10 meters/second, and impinging the melt stream onto a chill substrate, wherein a surface of the chill substrate moves past the orifice at a speed of between 12-50 meters/second.

Besides quenching molten metal (e.g., chill block melt spinning), amorphous metal alloys can be formed by sputter-depositing metals onto a substrate, ion-implantation, and solid-phase reaction. Each of these methods has its advantages and disadvantages. The choice of a particular method of fabrication depends on many variables, such as process compatibility and desired end use of the amorphous metal alloy article.

In some embodiments of the invention, amorphous metal alloy components for stents may be used. These components may be provided in a variety of ways. For example, the component may be produced by machining or processing amorphous metal alloy stock (e.g., a wire, ribbon, rod, tube, disk, and the like). Amorphous metal alloy stock made by chill block melt spinning can be used for such purposes.

It should be understood that the above description is only representative of illustrative examples of embodiments. For the reader's convenience, the above description has focused on a representative sample of possible embodiments, a sample that teaches the principles of the invention. Other embodiments may result from a different combination of portions of different embodiments. The description has not attempted to exhaustively enumerate all possible variations.

The invention claimed is:

1. A stent comprising a helical main stent component and a polymer material, wherein said main stent component comprises:
  a) a first side band having a first end and a second end, and a second side band having a first end and a second end, wherein the first and second side bands each have an undulating pattern and are connected to each other by cross-struts, wherein the first end of the first side band tapers toward the second side band at a first point of connection, and the first end of the second side band tapers toward the first side band at a second point of connection; wherein the second end of the first side band extends from the second point of connection, and the second end of the second end band extends from the first point of connection; and
  b) a first hook extending from the first side band and connected to the second end of the second side band; and a second hook extending from the second side band and connected to the second end of the first side band.

2. A stent comprising:
  a first side band having a first end and a second end;
  a second side band having a first end and a second end, the second side band being connected to the first side band to form cells therebetween;
  a first end band extending from the first end of the first side band;
  a second end band extending from the second end of the second side band;
  a first hook extending from the second side band in a first direction; and
  a second hook extending from the first side band in a second direction opposite the first direction.

3. The stent according to claim 2, wherein the first hook extends from a first end to a second, free end and comprises first and second members, the first member extending from the first end of the first hook at a first angle and the second member extending from the first member to the second end of the first hook at a second angle relative to the first member.

4. The stent according to claim 3, wherein the first end of the first hook is coupled to the second side band, the first hook being positioned and oriented such that the second end of the first hook aligns with the second end of the first end band in a tubular form of the stent.

5. The stent according to claim 2, wherein the second hook extends from a first end to a second, free end and comprises first and second members, the first member extending from the first end of the second hook at a first angle and the second member extending from the first member to the second end of the second hook at a second angle relative to the first member.

6. The stent according to claim 5, wherein the first end of the second hook is coupled to the first side band, the second hook being positioned and oriented such that the second end of the second hook aligns with the second end of the second end band in a tubular form of the stent.

7. The stent according to claim 2, wherein the first end band and the first hook form a first cylinder in the tubular form of the stent and the second end band and the second hook form a second cylinder in the tubular form of the stent.

8. The stent according to claim 7, wherein the first and second cylinders are right cylinders.

9. The stent according to claim 3, wherein the first end of the first end band is connected to the first side band at a point where the second side band tapers to connect with the first side band.

10. The stent according to claim 2, wherein the first end band extends substantially parallel to the first side band.

11. The stent according to claim 2, wherein the first end of the second end band is connected to the second side band at a point where the first side band tapers to connect with the second side band.

12. The stent according to claim 2, wherein the second end band extends substantially parallel to the second side band.

13. The stent according to claim 2, wherein the first and second side bands have an undulating pattern.

14. The stent according to claim 2, wherein the first and second end bands have an undulating pattern.

15. The stent according to claim 2, wherein the first and second hooks are connected to the second and first side bands, respectively, via welding.

16. The stent according to claim 2, wherein said cells decrease in area toward free ends of the stent.

17. The stent according to claim 2, wherein the first and second side bands are helically wound.

18. The stent according to claim 2, wherein the first side band is connected to the second side band via a plurality of struts.

19. A stent comprising:
a first side band having an undulating pattern and extending between a first end and a second end;
a second side band having an undulating pattern and extending between a first end and a second end, the second side band being connected to the first side band to form cells therebetween;
a first end band having an undulating pattern and extending from the first end of the first side band;
a second end band having an undulating pattern and extending from the second end of the second side band;
a first hook comprising a first end and a second end, said first end of said first hook coupled to the second side band, said first hook further comprising first and second members, the first member extending from the first end of the first hook and the second member extending at an angle from the first member, wherein the angle is an acute angle; and
a second hook comprising a first end and a second end, said first end of said second hook coupled to the first side band, said second hook comprising further third and fourth members, the third member extending from the first end of the second hook and the fourth member extending at an angle from the third member, wherein the angle is an acute angle.

20. The stent of claim 19, wherein the first hook is positioned at a first end of the stent in the tubular form and the second hook is positioned at a second end of the stent in the tubular form.

* * * * *

UNITED STATES PATENT AND TRADEMARK OFFICE
CERTIFICATE OF CORRECTION

PATENT NO. : 9,039,755 B2  
APPLICATION NO. : 13/829153  
DATED : May 26, 2015  
INVENTOR(S) : Jacob Richter Page 1 of 1

It is certified that error appears in the above-identified patent and that said Letters Patent is hereby corrected as shown below:

Claims
Column 18, Claim 1, line 38, please amend "second end of the second end band" to read "second end of the second side band"

Signed and Sealed this
Twenty-first Day of June, 2016

Michelle K. Lee
*Director of the United States Patent and Trademark Office*